US010780095B2

(12) United States Patent
Zhou

(10) Patent No.: US 10,780,095 B2
(45) Date of Patent: Sep. 22, 2020

(54) COMPOSITIONS AND METHODS FOR TREATING DISORDERS OF CIRCADIAN AND DIURNAL RHYTHMS USING PROKINETICIN 2 AGONISTS AND ANTAGONISTS

(71) Applicant: THE REGENTS OF THE UNIVERSITY OF CALIFORNIA, Oakland, CA (US)

(72) Inventor: Qun-Yong Zhou, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/090,044

(22) PCT Filed: Apr. 6, 2017

(86) PCT No.: PCT/US2017/026387
§ 371 (c)(1),
(2) Date: Sep. 28, 2018

(87) PCT Pub. No.: WO2017/177026
PCT Pub. Date: Oct. 12, 2017

(65) Prior Publication Data
US 2019/0117668 A1 Apr. 25, 2019

Related U.S. Application Data

(60) Provisional application No. 62/319,009, filed on Apr. 6, 2016.

(51) Int. Cl.
A61K 31/5513 (2006.01)
A61K 9/00 (2006.01)
A61K 45/06 (2006.01)
C07D 321/10 (2006.01)
C07D 405/12 (2006.01)
A61K 31/357 (2006.01)
C07D 413/12 (2006.01)
A61K 31/4025 (2006.01)
A61K 31/454 (2006.01)
A61K 31/5377 (2006.01)
A61K 31/4184 (2006.01)
A61P 37/06 (2006.01)
A61P 25/18 (2006.01)
A61P 25/24 (2006.01)
A61P 29/00 (2006.01)
A61P 35/00 (2006.01)

(52) U.S. Cl.
CPC ........ *A61K 31/5513* (2013.01); *A61K 9/0019* (2013.01); *A61K 9/0043* (2013.01); *A61K 9/0048* (2013.01); *A61K 31/357* (2013.01); *A61K 31/4025* (2013.01); *A61K 31/4184* (2013.01); *A61K 31/454* (2013.01); *A61K 31/5377* (2013.01); *A61K 45/06* (2013.01); *C07D 321/10* (2013.01); *C07D 405/12* (2013.01); *C07D 413/12* (2013.01); *A61P 25/18* (2018.01); *A61P 25/24* (2018.01); *A61P 29/00* (2018.01); *A61P 35/00* (2018.01); *A61P 37/06* (2018.01)

(58) Field of Classification Search
CPC .............. A61K 31/5513; A61K 9/0019; A61K 9/0043; A61K 9/0048; A61K 31/357; A61K 31/4025; A61K 31/4184; A61K 31/454; A61K 31/5377; A61K 45/06; C07D 321/10; C07D 405/12; C07D 413/12
USPC ....................................... 514/221
See application file for complete search history.

(56) References Cited

U.S. PATENT DOCUMENTS

| 2003/0235535 A1 | 12/2003 | Zhou et al. |
| 2006/0172935 A1 | 8/2006 | Zhou et al. |
| 2008/0287445 A1 | 11/2008 | Coats et al. |
| 2012/0035149 A1 | 2/2012 | Zhou et al. |

FOREIGN PATENT DOCUMENTS

WO 2007067511 A2 6/2007

OTHER PUBLICATIONS

Patel et al., Ocular drug delivery systems: An overview, Jan. 12, 2015, World J Pharmacol. Author manuscript, pp. 1-35 (Year : 2015).*
Zhou et al., "Prokineticin 2 and circadian clock output" FEBS Journal, Wiley-Blackwell Publishing Ltd., GB, 2005, v 272, n 22, p. 5703-5709.
Cheng et al., "Prokineticin 2 transmits the behavioural circadian rhythm of the suprachiasmatic nucleus" Nature Publishing Group, 2002, v 417, p. 405-410.
Li et al., "Disruption of the circadian output molecule prokineticin 2 results in anxiolytic and antidepressant-like effects in mice" Neuropsychopharmrmacology, 2009, v 34, p. 367-373.
Olioso et al., "Effects of gelsemium sempervirens L. on pathway-focused gene expression profiling in neuronal cells" Journal of Ethnopharmacology, 2014, v, 153, n 2, p. 535-539.
Buttner, Supplementary European Search Report for corresponding European Patent Application EP 17779838, dated Oct. 11, 2019.
Buttner, Extended European Search Report for corresponding European Patent Application EP 17779838, dated Jan. 23, 2020.

* cited by examiner

*Primary Examiner* — Kristin A Vajda
(74) *Attorney, Agent, or Firm* — Greer, Burns & Crain, Ltd.; Gregory P. Einhorn

(57) ABSTRACT

In alternative embodiments, provided are methods for: modifying circadian rhythmicity or timing in a mammal, treating psychiatric conditions or symptoms due to alterations in a human circadian regulatory system, treating sleep problems in a mammal, or inducing sleep or activity suppression, or causing an arousal or wakening reaction, comprising administration to a mammal or human a compound or composition capable of modifying a prokineticin 2 (PK2) expression or activity, and/or a PKR2 (PK2 receptor), a vasopressin receptor (VR), and/or a melatonin receptor (MR) expression or activity.

9 Claims, 23 Drawing Sheets

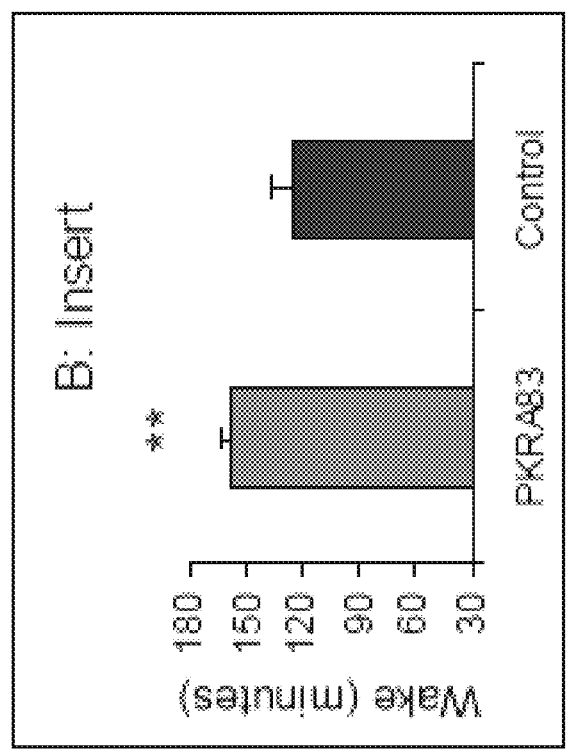
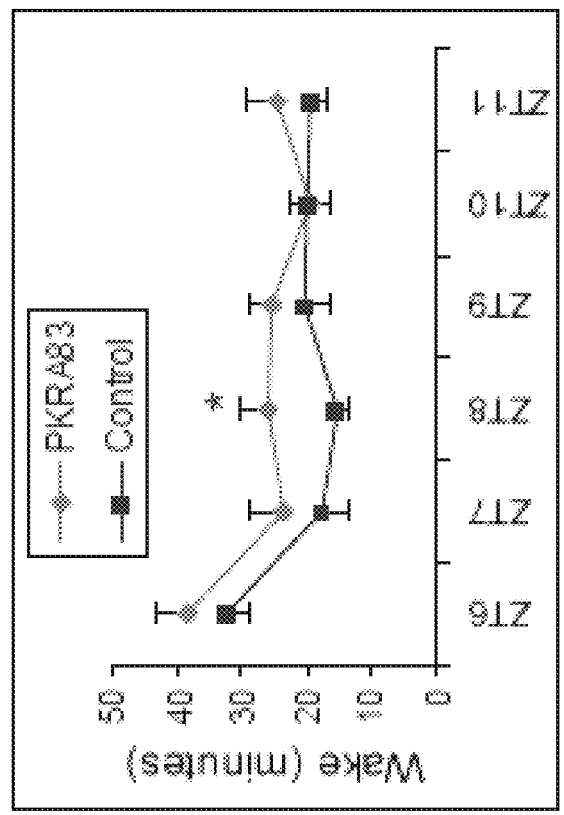
Fig. 6B

Fig. 7
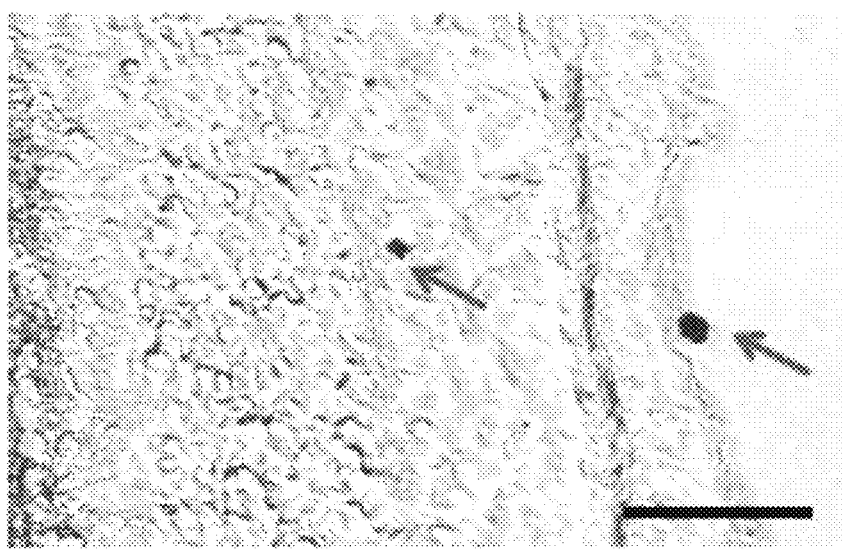
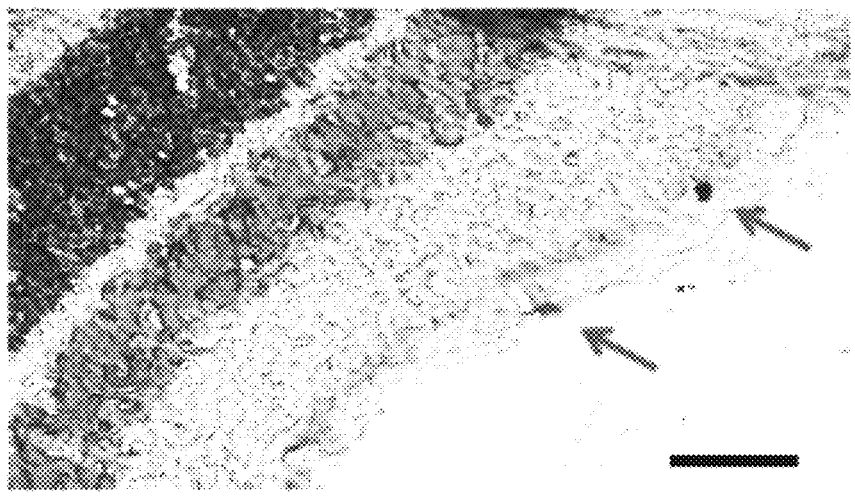

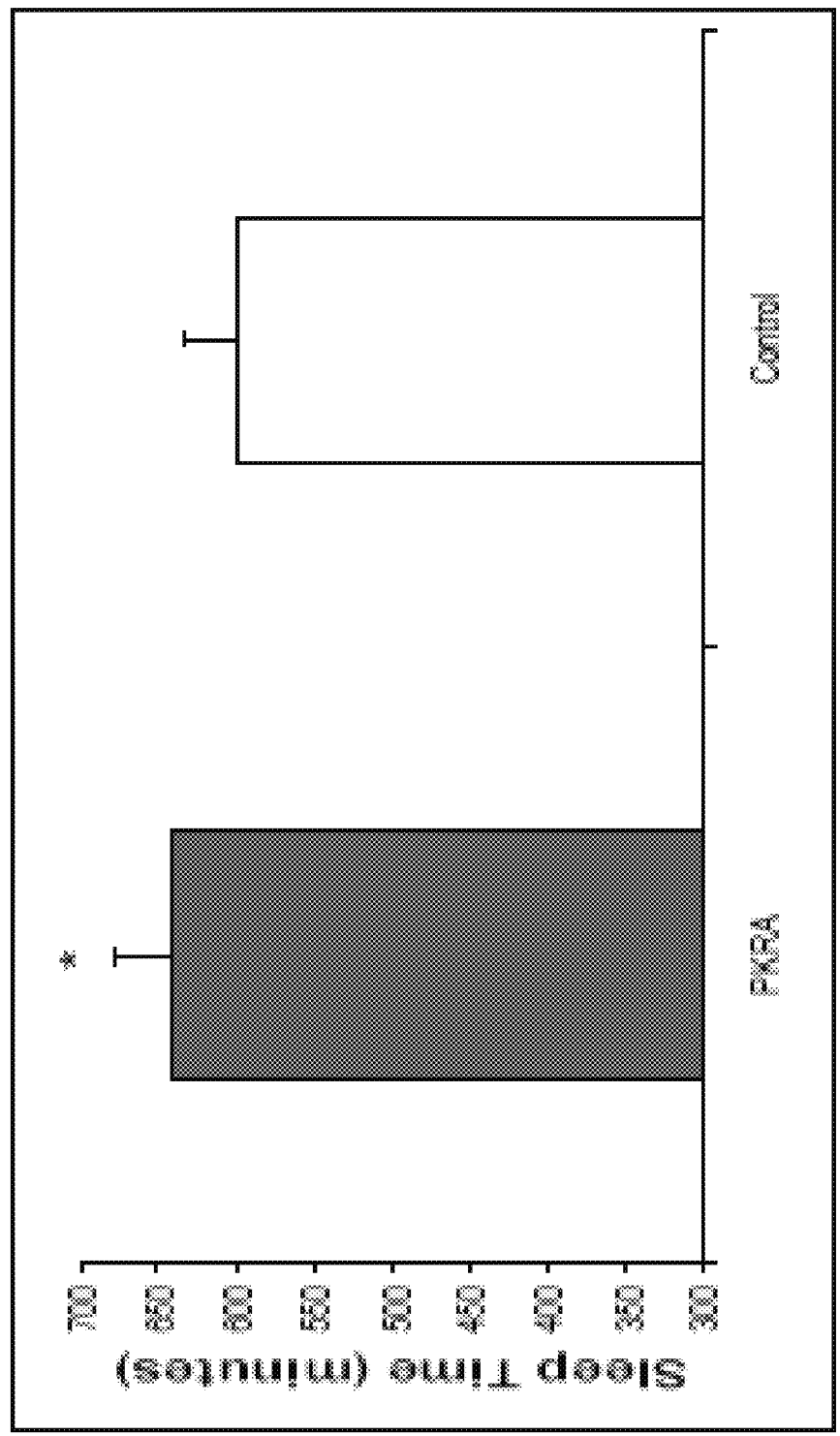

COMPOSITIONS AND METHODS FOR TREATING DISORDERS OF CIRCADIAN AND DIURNAL RHYTHMS USING PROKINETICIN 2 AGONISTS AND ANTAGONISTS

STATEMENT AS TO FEDERALLY SPONSORED RESEARCH

This application is a national phase application claiming benefit of priority under 35 U.S.C. § 371 to International (PCT) Patent Application serial number PCT/US2017/026387, filed Apr. 6, 2017, now pending, which claims priority from patent application U.S. Ser. No. 62/319,009, filed Apr. 6, 2016, the contents of which are incorporated herein in entirety. The aforementioned applications are expressly incorporated herein by reference in their entirety and for all purposes.

STATEMENT AS TO FEDERALLY SPONSORED RESEARCH

This invention was made with government support under grant no. DK091916, awarded by the National Institutes of Health. The government has certain rights in the invention.

TECHNICAL FIELD

This invention generally relates to neuro- and photobiology and mammalian behavior dependent on diurnal rhythms. In alternative embodiments, provided compositions and methods for: modifying circadian rhythmicity or timing in a mammal, treating psychiatric conditions or symptoms due to alterations in a human circadian regulatory system, treating sleep problems in a mammal, or inducing sleep or activity suppression, or causing an arousal or wakening reaction, comprising administration to a mammal or human a compound or composition capable of modifying a prokineticin 2 (PK2) expression or activity, and/or a PKR2 (PK2 receptor), a vasopressin receptor (VR), and/or a melatonin receptor (MR) expression or activity. In alternative embodiments, administration of a PK2 agonist or a compound, or composition increases or activates prokineticin 2 (PK2), a PKR2 (PK2 receptor), a VR activity, and/or a MR activity causes or results in an arousal or wakening reaction by a mammal, and administration of a PK2 antagonist or a compound or composition decreases or de-activates prokineticin 2 (PK2), a PKR2 (PK2 receptor), a VR activity, and/or a MR activity causes or results in activity suppression and sleep induction in a mammal.

BACKGROUND

About 2% population suffer from some forms of circadian rhythm disorders with sleep or mood symptoms. Other examples of circadian rhythm sleep disorders include jet lag and shift worker syndrome, which are associated with dysregulation of the internal circadian system with respect to the external environment. Another example of a circadian rhythm sleep disorder is Advanced Sleep Phase Disorder (ASPD), which is characterized by early evening bedtimes and early morning awakenings (approximately 2-5 am). Sleep problems are common in general population, particularly for elders. Many elders report early morning awakenings, with some symptoms similar to ASPD.

Disturbances in circadian rhythmicity or timing have profound effects on the mood, in addition to symptoms of sleep. It is now recognized that the high prevalence of circadian abnormalities in psychiatric disorders is not only a consequence of psychiatric symptoms but also due to alterations in the circadian regulatory system. Typical treatment for seasonal affective disorders includes antidepressant medications and light therapy. Evidence for the effectiveness of antidepressant for seasonal affective disorders is limited. Light therapy, particularly with blue light, appears effective for seasonal affective disorders. However, light therapy is cumbersome and time-consuming, and is not possible to become a standard therapy for most subjects with chronic or recurring disorders such as seasonal affective disorders.

Suprachiasmatic nucleus (SCN) has been thought to house the master circadian clock for all species of mammals. Supporting evidence for such claim is overwhelmingly strong for the nocturnal mammals, such as mice and rats. However, the same claim that SCN houses the master clocks for circadian wakefulness level regulation has actually limited supporting evidence in the case of the diurnal animals, human being included. The well cited work of increased sleep by SCN lesion in squirrel monkeys (Edgar et al., 1993), interpreted as the wakefulness or arousal-promoting of the SCN for the diurnal animals could be due to concurrent lesions to the retino-hypothalamic tract. Thus, sites other than the SCN may house the critical circadian clock(s) that regulates the wakefulness levels for the diurnal animals, such as the primates, including human beings.

SUMMARY

In alternative embodiments, provided are compositions, products of manufacture and methods for modifying circadian rhythmicity or timing in a mammal, and treating, ameliorating, or preventing, disorders of circadian and diurnal rhythms using prokineticin 2 agonists and antagonists.

In alternative embodiments, provided are compounds having a structure as set forth in Table 1, or equivalents thereof, or a stereoisomer thereof, or an analog thereof, or a pharmaceutically acceptable salt thereof, or a bioisostere thereof, wherein the compound, equivalents thereof, stereoisomer thereof, analog thereof, pharmaceutically acceptable salt thereof, or bioisostere thereof acts as a PK2 antagonist, or a compound or composition capable of decreasing activity of or de-activating prokineticin 2 (PK2), or acting as a PK2 receptor antagonist.

In alternative embodiments, provided are formulations comprising a compound or composition as provided herein, wherein optionally the formulation is a solid, semi-solid, liquid, aerosol, powder or emulsion formulation.

In alternative embodiments, provided are pharmaceutical compositions comprising a compound or composition as provided herein, wherein optionally the pharmaceutical composition is formulated for enteral or parenteral administration, and optionally the compound is formulated for administration in vivo; or for enteral or parenteral administration, or as an ointment, a tablet, pill, capsule, gel, geltab, liquid, lotion, aerosol or implant, and optionally the compound is formulated as a nanoparticle or a nanolipoparticle.

In alternative embodiments, provided are methods for:
modifying circadian rhythmicity or timing in a mammal,
treating or ameliorating a psychiatric condition or a symptom due to alterations in, or caused by a dysfunction or a genetic defect in, or a non-wild type pattern of or biofeedback mechanism in, a human circadian regulatory system, treating or ameliorating a neuropsychiatric disorder linked to regulation of circadian rhythm, treating or ameliorating sleep problems or a sleep disorder in a mammal, inducing sleep or activity suppression, or causing an arousal or wakening reaction, treating or ameliorating photophobia, or treating or ameliorating attention-deficit/hyperactivity disorder (ADHD), treating, preventing or ameliorating symptom of acute or chronic pain, treating, preventing or ameliorating a cancer, wherein optionally the cancer is a glioblastoma or a pancreatic cancer, treating, preventing or ameliorating an inflammatory disease, wherein optionally the inflammatory disease is psoriasis or arthritis, comprising:

(a) providing a compound or composition capable of acting as an agonist or an antagonist for:

(1) modifying prokineticin 2 (PK2) activity,
(2) modifying PKR2 (PK2 receptor) activity,
(3) modifying a vasopressin receptor (VR) activity, wherein optionally the VR is a V1a or V1b type VR, or
(4) modifying a melatonin receptor (MR) activity; and (b) administering one or any combination of a compound or composition of (a) to a mammal or a human in need thereof, wherein optionally the combination comprises an agonist or an antagonist of: PKR2 and VR; PKR2 and MR; PKR2 and PK2; VR and PK2; MR and PK2; MR and VR; or, PKR2, VR and MR, and optionally the prokineticin (PK2) receptor antagonist is a compound as set forth in U.S. Pat. No. 8,722,896, or a compound having a structure as set forth in Formula 1, or a compound as provided herein; or a compound as described in U.S. Pat. App. Pub. No. 2015/0111922; or U.S. Pat. App. Pub. No. 2014/0038968; or U.S. Pat. No. 7,855,201 (or WO2007067511, PCT/US2006/046330), and optionally the melatonin receptor (MR) antagonist is a compound as set forth in U.S. Pat. No. 8,907,126, or WO/2014/103998, and optionally the vasopressin receptor (VR) antagonist is a compound as set forth in US 2016-0221944 A1, US 2015-0073032 A1, or WO/2015/036160, wherein administration of a PK2 agonist or a compound or composition capable of increasing or activating prokineticin 2 (PK2) or a PKR2 (PK2 receptor) causes or results in an arousal or wakening reaction by the human or mammal, wherein administration of a VR agonist or a compound or composition capable of increasing or activating a VR activity causes or results in an arousal or wakening reaction by the human or mammal, wherein administration of a MR agonist or a compound or composition capable of increasing or activating a MR activity causes or results in an arousal or wakening reaction by the human or mammal, administration of a PK2 antagonist or a compound or composition capable of decreasing or de-activating prokineticin 2 (PK2) or a PKR2 (PK2 receptor) causes or results in activity suppression and sleep induction in the human or mammal, administration of a VR antagonist or a compound or composition capable of decreasing or de-activating a VR activity causes or results in activity suppression and sleep induction in the human or mammal, administration of a MR antagonist or a compound or composition capable of decreasing or de-activating a MR activity causes or results in activity suppression and sleep induction in the human or mammal, and administration of an antagonist or a compound or composition capable of decreasing or de-activating a prokineticin 2 (PK2), a PKR2 (PK2 receptor), a VR activity, and/or a MR activity causes or results in:

treating or ameliorating a neuropsychiatric disorder linked to regulation of circadian rhythm, treating or ameliorating photophobia, or treating or ameliorating attention-deficit/hyperactivity disorder (ADHD), treating, preventing or ameliorating symptom of acute or chronic pain, treating, preventing or ameliorating a cancer, wherein optionally the cancer is a glioblastoma or a pancreatic cancer, treating, preventing or ameliorating an inflammatory disease, wherein optionally the inflammatory disease is psoriasis or arthritis.

In alternative embodiments, the neuropsychiatric disorder linked to regulation of circadian rhythm: a mood disorder; depression; jet lag; shift worker syndrome; Advanced Sleep Phase Disorder (ASPD); seasonal affective disorder (SAD); familial advanced sleep phase syndrome; a circadian rhythm sleep disorder of a delayed sleep phase type, an irregular sleep-wake type or a non-24-hour sleep-wake type.

In alternative embodiments, the compound or composition is formulated as a pharmaceutical composition, optionally formulated for enteral or parenteral administration, optionally formulated for administration in vivo or for oral, mucosal or intranasal administration, optionally formulated as an ointment, a tablet, pill, capsule, gel, ointment, geltab, syrup, slurry, suspension, liquid, lotion, aerosol or implant, and optionally the compound is formulated as a particle, a liposome, a nanoparticle or a nanolipoparticle.

In alternative embodiments, the compound or composition is formulated for injection, optionally by subcutaneous (IC), intramuscular (IM), intravenous (IV) and/or intradermal injection or infusion. In alternative embodiments, the compound or composition is formulated for topical or mucosal administration, optionally formulated as a gel, a topical, an ointment, a spray, an eye drop or ointment. In alternative embodiments, the composition, compound or formulation is administered orally, parenterally, by inhalation spray, nasally, topically, intrathecally, intrathecally, intracerebrally, epidurally, intracranially or rectally.

In alternative embodiments, the agonist or antagonist composition or compound is an antibody that specifically binds to a prokineticin 2 (PK2), a PKR2 (PK2 receptor), a vasopressin receptor (VR), or a melatonin receptor (MR), and either inhibits PK2, PKR2, VR or MR activity or expression, or increases or sustains PK2, PKR2, VR or MR activity or expression.

In alternative embodiments, the agonist or antagonist composition or compound is a nucleic acid that specifically binds to a prokineticin 2 (PK2), a PKR2 (PK2 receptor), a vasopressin receptor (VR), or a melatonin receptor (MR) gene or transcript, and/or either inhibits PK2, PKR2, VR or MR activity or expression, or increases or sustains PK2, PKR2, VR or MR activity or expression, and optionally the antagonist is an inhibitory nucleic acid, wherein optionally the inhibitory nucleic acid is an siRNA or an antisense oligonucleotide.

In alternative embodiments, wherein the agonist or antagonist composition or compound is a small molecule, a protein, a peptide, a carbohydrate or a lipid that specifically binds to a prokineticin 2 (PK2), a PKR2 (PK2 receptor), a vasopressin receptor (VR), or a melatonin receptor (MR) gene or transcript, and/or either inhibits PK2, PKR2, VR or MR activity or expression, or increases or sustains PK2, PKR2, VR or MR activity or expression.

In alternative embodiments, provided are therapeutic combinations for
- modifying circadian rhythmicity or timing in a mammal,
- treating or ameliorating a psychiatric condition or a symptom due to alterations in, or caused by a dysfunction or a genetic defect in, or a non-wild type pattern of or biofeedback mechanism in, a human circadian regulatory system,
- treating or ameliorating a neuropsychiatric disorder linked to regulation of circadian rhythm,
- treating or ameliorating sleep problems or a sleep disorder in a mammal,
- inducing sleep or activity suppression, or causing an arousal or wakening reaction,
- treating or ameliorating photophobia, or
- treating or ameliorating attention-deficit/hyperactivity disorder (ADHD),
- treating, preventing or ameliorating symptom of acute or chronic pain,
- treating, preventing or ameliorating a cancer, wherein optionally the cancer is a glioblastoma or a pancreatic cancer,
- treating, preventing or ameliorating an inflammatory disease, wherein optionally the inflammatory disease is psoriasis or arthritis, wherein the therapeutic combination comprises two or more compounds or compositions, where the two or more compounds or compositions is capable of at least one of:
  (1) modifying prokineticin 2 (PK2) activity,
  (2) modifying PKR2 (PK2 receptor),
  (3) modifying a vasopressin receptor (VR) activity, wherein optionally the VR is a V1a or V1b type VR, or
  (4) modifying a melatonin receptor (MR) activity; and
  wherein optionally the combination comprises an agonist or an antagonist of: PKR2 and VR; PKR2 and MR; PKR2 and PK2; VR and PK2; MR and PK2; or, PKR2, VR and MR,
  and optionally the prokineticin (PK2) receptor antagonist is a compound as set forth in U.S. Pat. No. 8,722,896, or a compound having a structure as set forth in Formula 1, or a compound as provided herein; or a compound as described in U.S. Pat. App. Pub. No. 2015/0111922; or U.S. Pat. App. Pub. No. 2014/0038968; or U.S. Pat. No. 7,855,201 (or WO2007067511, PCT/US2006/046330),
  and optionally the melatonin receptor (MR) antagonist is a compound as set forth in U.S. Pat. No. 8,907,126, or WO/2014/103998,
  and optionally the vasopressin receptor (VR) antagonist is a compound as set forth in US 2016-0221944 A1, US 2015-0073032 A1, or WO/2015/036160.

In alternative embodiments, provided are kits comprising: a composition as provided herein, a formulation as provided herein, a pharmaceutical composition as provided herein, a therapeutic combination as provided herein, or a compound or composition is capable of at least one of:
  (1) modifying prokineticin 2 (PK2) activity,
  (2) modifying PKR2 (PK2 receptor),
  (3) modifying a vasopressin receptor (VR) activity, wherein optionally the VR is a V1a or V1b type VR, or
  (4) modifying a melatonin receptor (MR) activity; and
  wherein optionally the combination comprises an agonist or an antagonist of: PKR2 and VR; PKR2 and MR; PKR2 and PK2; VR and PK2; MR and PK2; or, PKR2, VR and MR,
  and optionally the prokineticin (PK2) receptor antagonist is a compound as set forth in U.S. Pat. No. 8,722,896, or a compound having a structure as set forth in Formula 1, or a compound as provided herein; or a compound as described in U.S. Pat. App. Pub. No. 2015/0111922; or U.S. Pat. App. Pub. No. 2014/0038968; or U.S. Pat. No. 7,855,201 (or WO2007067511, PCT/US2006/046330),
  and optionally the melatonin receptor (MR) antagonist is a compound as set forth in U.S. Pat. No. 8,907,126, or WO/2014/103998,
  and optionally the vasopressin receptor (VR) antagonist is a compound as set forth in US 2016-0221944 A1, US 2015-0073032 A1, or WO/2015/036160.

In alternative embodiments, provided are products of manufacture comprising: a composition as provided herein, a formulation as provided herein, a pharmaceutical composition as provided herein, a therapeutic combination as provided herein, or a compound or composition is capable of at least one of:
  (1) modifying prokineticin 2 (PK2) activity,
  (2) modifying PKR2 (PK2 receptor),
  (3) modifying a vasopressin receptor (VR) activity, wherein optionally the VR is a V1a or V1b type VR, or
  (4) modifying a melatonin receptor (MR) activity;
  wherein optionally the combination comprises an agonist or an antagonist of: PKR2 and VR; PKR2 and MR; PKR2 and PK2; VR and PK2; MR and PK2; or, PKR2, VR and MR,
  and optionally the prokineticin (PK2) receptor antagonist is a compound as set forth in U.S. Pat. No. 8,722,896, or a compound having a structure as set forth in Formula 1, or a compound as provided herein; or a compound as described in U.S. Pat. App. Pub. No. 2015/0111922; or U.S. Pat. App. Pub. No. 2014/0038968; or U.S. Pat. No. 7,855,201 (or WO2007067511, PCT/US2006/046330),
  and optionally the melatonin receptor (MR) antagonist is a compound as set forth in U.S. Pat. No. 8,907,126, or WO/2014/103998,
  and optionally the vasopressin receptor (VR) antagonist is a compound as set forth in US 2016-0221944 A1, US 2015-0073032 A1, or WO/2015/036160,
  and optionally the product of manufacture is a kit, a pump, a device, a subcutaneous infusion device, a continuous subcutaneous infusion device, an infusion pen, a needle, a reservoir, an ampoules, a vial, a syringe, a cartridge, a pen, a disposable pen or jet injector, a prefilled pen or a syringe or a cartridge, a cartridge or a disposable pen or jet injector, a two chambered or multi-chambered pump.

In alternative embodiments, provided are Uses of: a composition as provided herein, a formulation as provided herein, a pharmaceutical composition as provided herein, a therapeutic combination as provided herein, or a compound or composition is capable of at least one of:
  (1) modifying prokineticin 2 (PK2) activity,
  (2) modifying PKR2 (PK2 receptor),
  (3) modifying a vasopressin receptor (VR) activity, wherein optionally the VR is a V1a or V1b type VR, or
  (4) modifying a melatonin receptor (MR) activity;
  in the manufacture of a medicament,
  and optionally the use is for:
  modifying circadian rhythmicity or timing in a mammal,
  treating or ameliorating a psychiatric condition or a symptom due to alterations in, or caused by a dysfunction or a genetic defect in, or a non-wild type pattern of or biofeedback mechanism in, a human circadian regulatory system, treating or ameliorating a neuropsychiatric disorder linked to regulation of circadian rhythm, treating or ameliorating sleep problems or a sleep disorder in a mammal, inducing sleep or activity suppression, or causing an arousal or wakening reaction, treating or ameliorating photophobia, or treating or ameliorating attention-deficit/hyperactivity disorder (ADHD), treating, preventing or ameliorating symptom of acute or chronic pain, treating, preventing or ameliorating a cancer, wherein optionally the cancer is a glioblastoma or a pancreatic cancer, treating, preventing or ameliorating an inflammatory disease, wherein optionally the inflammatory disease is psoriasis or arthritis.

In alternative embodiments, provided are compounds, formulae, products of manufacture or compositions for use as a medicament, and optionally the medicament is used for:

modifying circadian timing in a mammal, treating or ameliorating a psychiatric condition or a symptom due to alterations in, or caused by a dysfunction or a genetic defect in, or a non-wild type pattern of or biofeedback mechanism in, a human circadian regulatory system, treating or ameliorating a neuropsychiatric disorder linked to regulation of circadian rhythm, treating or ameliorating sleep problems or a sleep disorder in a mammal, inducing sleep or activity suppression, or causing an arousal or wakening reaction, treating or ameliorating photophobia, or treating or ameliorating attention-deficit/hyperactivity disorder (ADHD), treating, preventing or ameliorating symptom of acute or chronic pain, treating, preventing or ameliorating a cancer, wherein optionally the cancer is a glioblastoma or a pancreatic cancer, treating, preventing or ameliorating an inflammatory disease, wherein optionally the inflammatory disease is psoriasis or arthritis, and the compound, formula, product of manufacture or composition comprises: a composition as provided herein, a formulation as provided herein, a pharmaceutical composition as provided herein, a therapeutic combination as provided herein, or a compound or composition is capable of at least one of:

(1) modifying prokineticin 2 (PK2) activity,
(2) modifying PKR2 (PK2 receptor),
(3) modifying a vasopressin receptor (VR) activity, wherein optionally the VR is a V1a or V1b type VR, or
(4) modifying a melatonin receptor (MR) activity;

or a kit o as provided herein, or a product of manufacture as provided herein.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

FIG. 1A, showing activity counts as a function of light or dark exposure, when a light pulse (150 lux) was administrated to wild type mice during the middle of dark period (as indicated as ZT16-ZT18.5), the locomotor activities were significantly suppressed, and in contrast, only marginal suppression of the locomotor activities by light pulses was observed for the PK2−/− mice; FIG. 1B, showing wake time in minutes as a function of light or dark exposure, EEG/EMG recording revealed that light pulses suppressed wakefulness in the wild type mice, or the PK2−/− mice, as described in detail in Example 1, below.

FIG. 3A shows PK2 is strongly expressed in some retinal ganglion cells, and further co-immunostaining studies indicated that all OPN4-positive retinal ganglion cells express PK2, (FIG. 3B); FIG. 3C shows an image of Hoeschst staining (which stains DNA), and FIG. 3D is a merged image of FIG. 3A-C, as described in detail in Example 1, below.

FIG. 4A, showing PK2 staining in monkey ipRGC; FIG. 4B showing OPN4 staining in the same retinal ganglion cells; FIG. 4C showing Hoeschst staining in the retinal ganglion cells; and FIG. 4D is a merged image of FIG. 4A-C showing that PK2 is co-expressed with OPN4 in the monkey ipRGC, as described in detail in Example 1, below.

FIG. 5A shows PKR2 staining, showing PKR2 is only expressed in the dorsal SCN, but is not detected in the ventral SCN of monkey brain; FIG. 5B, shows PKR2 staining, showing PKR2 is expressed in the entire SCN, covering both the ventral and dorsal compartments of the SCN of mouse brain: FIG. 5C, shows PKR2 staining, showing PKR2 was robustly expressed in the superficial layer of the SC in the monkey brain; FIG. 5D, shows PKR2 staining, showing PKR2 expression was not detected in the SC of the mouse brain, as described in detail in Example 1, below.

FIG. 6A-C graphically illustrate data from studies that examined the effect of a synthetic PK2 antagonist, PKRA83, on the arousal levels in the mice and the monkeys: FIG. 6A and FIG. 6B, illustrate data showing that administration of PKRA83 significantly increased the locomotor activity (FIG. 6A) and the wakefulness (FIG. 6B) in the mice; FIG. 6C illustrates data showing that administration of the PK2 antagonist in the monkeys resulted in a significant increase of the sleep time, as described in detail in Example 1, below.

FIG. 7A-B illustrates images showing the expression of PK2 in the retinal ganglion cells of the mouse retina; FIG. 7A are examples of two PK2-positive retinal ganglion cells, one nondisplaced and one displaced PK2-positive retinal ganglion cells are marked with arrows; FIG. 7B are examples of two PK2-positive retinal ganglion cells, one strongly and one more modestly stained, are marked with arrows, as described in detail in Example 1, below.

FIG. 10A, illustrates data and corresponding images of the immune-fluorescence intensity of PK2 as quantified and shown as mean±SEM; FIG. 10B illustrates data and corresponding images showing that the PK2 levels in the ipRGC of Bmal1-deficient mice (BMAL KO) were consistently low, and displayed no apparent oscillation; the Inserts above the columns show representative images of PK2 immunostaining of the ipRGC (green), and nuclear counterstaining is shown as blue, as described in detail in Example 1, below.

FIG. 11A shows the PKR2 signals in the retinal ganglion cell layer; FIG. 11B shows a higher magnification image of boxed area of FIG. 11A; in FIG. 11B individual retinal ganglion cells that are PKR2-positive are apparent; FIG. 11C and FIG. 11D show Nissl staining of eye sections corresponding to FIG. 11A and FIG. 11B, respectively, as described in detail in Example 2, below.

FIG. 19 graphically illustrates data of sleep time in PKRA-administered monkeys versus control (no antagonist), showing that nasal cavity application of PK2 receptor antagonist promoted sleep in the monkeys, as described in detail in Example 2, below.

Like reference symbols in the various drawings indicate like elements.

DETAILED DESCRIPTION

Figure 1A:
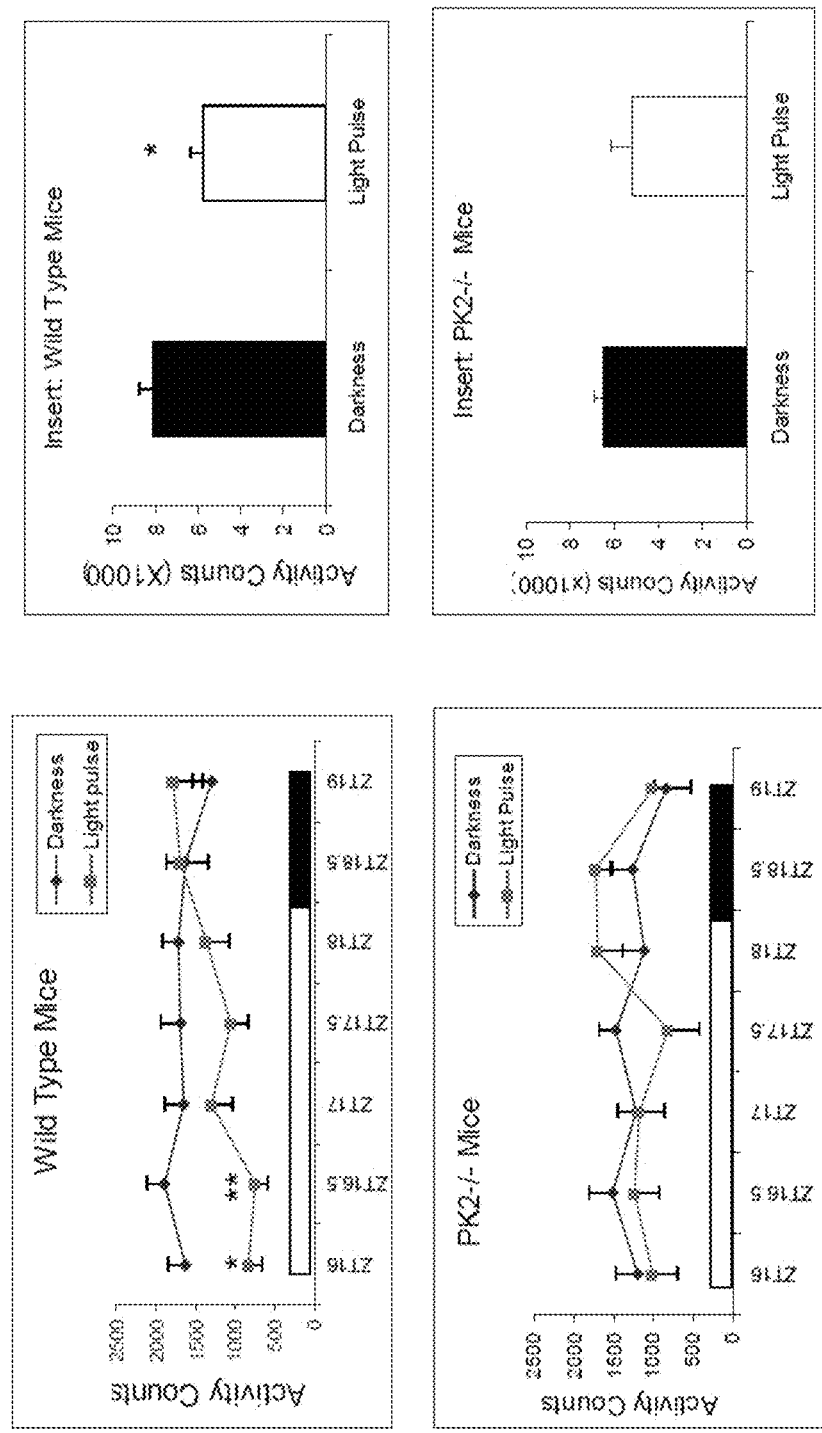
FIG. 1A-B graphically illustrate data from studies that examined the suppression effect of light pulses on the locomotor activities and the arousal levels in the PK2−/− mice.

In alternative embodiments, provided compositions and methods for: modifying circadian rhythmicity or timing in a mammal, treating psychiatric conditions or symptoms due to alterations in a human circadian regulatory system, treating sleep problems in a mammal, or inducing sleep or activity suppression, or causing an arousal or wakening reaction, comprising administration to a mammal or human a compound or composition capable of modifying prokineticin 2 (PK2) activity. While the invention is not limited by any particular mechanism of action, provided are compositions and methods that target and modify the activity or activation of, or the results of inhibition or activation of receptor signaling, of receptors expressed in intrinsically photosensitive retinal ganglion cells for the treatment of e.g., certain central nervous disorders such as seep, mood disorders and other neuropsychiatric disorders linked to regulations of circadian rhythms.

Described for the first time herein is that PK2 couples the intrinsically photosensitive retinal ganglion cells (ipRGC) and also signals to the brain targets of the ipRGC for the regulation of arousal levels and sleep/wake cycle. The molecular machinery and strategic location of the ipRGC enables ipRGC to integrate circadian clock information and environmental light/dark conditions. ipRGC project to brain centers, such as superior colliculus, that are critical for the regulation of the arousal levels and sleep wake cycle, particularly for the diurnal mammals, human beings included. Pharmacologic targeting of the ipRGC, specifically the receptors expressed in the ipRGC as provided herein provides gateways for treating the related central nervous disorders, particularly sleep and mood disorders, such as seasonal affective disorder, and bipolar disorders.

Described for the first time herein is the data showing that intrinsically photosensitive retinal ganglion cells (ipRGC), whose activity can be modified by modulation of prokineticin 2 (PK2) signaling, as described herein, are critical for the regulation of circadian rhythms in diurnal mammals for the regulation of wakefulness and sleep. Provided herein are methods for modulating PK2 signaling of the ipRGC for the regulation of wakefulness and sleep.

We have discovered that the intrinsically photosensitive retinal ganglion cells (ipRGC) house one of the master circadian clocks for the diurnal animals under ambient light dark conditions. Particularly, we have shown that prokineticin 2 (PK2), a clock output molecule, is expressed in the ipRGC of mouse (FIG. 3) and monkey (FIG. 4). ipRGC are the photic channels that mediate the light masking and the light entrainment. ipRGC sense light directly via their own photopigment and indirectly via the classic photoreceptors in the outer segment of the retina. The PK2 signaling from the ipRGC impinges on the retinorecipient compartment of the suprachiasmatic nucleus (ventral SCN), and also impinges on the superior colliculus (SC) of the midbrain. In the mouse brain, PKR2 (PK2 receptor) is robustly expressed in the retinorecipient SCN, but is essentially absent in the SC, thus the PK2 signaling funnels mainly through the ipRGC-SCN pathway. In contrast, PKR2 is not expressed in the retinorecipient ventral SCN of the monkey brain, but strongly expressed in the retinorecipient superficial layer of the SC. Thus, the PK2 signaling of the ipRGC in the monkey funnels via the ipRGC-SC pathway. Overall, the PK2 signaling is stimulatory for arousal level for the diurnal monkey and inhibitory for the nocturnal mouse (see FIG. 8, Example 1, below).

The ipRGC-SC pathway modulates the arousal level via projections to cortical areas that are routed through the lateral posterior/Pulvinar thalamus, or via the reticular activation system in the brain stem. The PK2 signaling of the ipRGC-SC pathway is likely to be stimulatory for the arousal levels of both the nocturnal mouse and the diurnal monkey. The arousal stimulation of the ipRGC-SC pathway by light is likely to be relatively minor (brief, but not sustained) in the nocturnal animals such as rats and mice. This is consistent with the absence of PKR2 (PK2 receptor) expression in the SC of the mouse brain. It is noticed that the overall size of the SC, the lateral positive/Pulvinar complex of the thalamus and associated cortices are all significantly enlarged and expanded in the diurnal mammals, such as primates, compared to the nocturnal mammals such as mice. PK2 pathway in the SCN (both the ventral and the dorsal) likely projects, directly or indirectly, to the arousal centers such as ventrolateral preoptic nucleus of the hypothalamus, lateral hypothalamus, and locus coeruleus. The PK2 signaling pathway, including PKR2 (PK2 receptor), of the ipRGC-SCN pathway is clearly inhibitory for the arousal levels of the nocturnal mouse. Our findings revealed that the mammalian diurnal/nocturnal determination is mediated by the differential signaling of the ipRGC onto their brain targets. PK2 in the monkey SCN is known to oscillate in the same phase as that of the mouse (Burton et al., 2016).

Products of Manufacture and Kits

Provided are products of manufacture and kits comprising a therapeutic combination as provided herein, or a compound or composition, e.g., a pharmaceutical composition, as provided herein, for: (1) modifying prokineticin 2 (PK2) activity, (2) modifying PKR2 (PK2 receptor), (3) modifying a vasopressin receptor (VR) activity, wherein optionally the VR is a V1a or V1b type VR, or (4) modifying a melatonin receptor (MR) activity; and wherein optionally the combination comprises an agonist or an antagonist of: PKR2 and VR; PKR2 and MR; PKR2 and PK2; VR and PK2; MR and PK2; or, PKR2, VR and MR.

In alternative embodiments, the kits further comprise instructions for practicing a method as provided herein.

The invention will be further described with reference to the examples described herein; however, it is to be understood that the invention is not limited to such examples.

EXAMPLES

Example 1: Novel Neural and Molecular Mechanisms for Mammalian Diurnal and Nocturnal Determination This example demonstrates that methods as provided herein are effective for modifying circadian rhythmicity or timing in a mammal, treating psychiatric conditions or symptoms due to alterations in a human circadian regulatory system, treating sleep problems in a mammal, or inducing sleep or activity suppression, or causing an arousal or wakening reaction. Described for the first time herein are novel neural and molecular mechanisms for mammalian diurnal and nocturnal determination. Here we demonstrate that prokineticin 2 (PK2), previously shown as an output molecule of the suprachiasmatic circadian clock, is expressed in the intrinsically photosensitive retinal ganglion cells, and the PK2 signaling is required for the activity and arousal suppression by light in the mouse. Between the nocturnal mouse and the diurnal monkey, a signaling receptor for PK2 is shown to be differentially expressed in the retino-recipient suprachiasmatic nucleus and the superior colliculus, brain projection targets of the intrinsically photosensitive retinal ganglion cells. Blockade with a selective antagonist reveals the respectively inhibitory and stimulatory effect of PK2 signaling on the arousal levels for the nocturnal mouse and the diurnal monkey. Thus, the mammalian diurnality or nocturnality is determined by the differential signaling of PK2 from the intrinsically photosensitive retinal ganglion cells onto their retinorecipient brain targets.

In this Example, we show that PK2, a molecule previously shown as an important SCN output signal, is co-expressed with melanopsin (OPN4) in the intrinsically photosensitive retinal ganglion cells (ipRGC). We further show that PK2 signaling is required for sustained light-induced activity suppression and sleep induction in mice. Blockade with PK2 antagonist demonstrated the opposite effects of the PK2 signaling on the arousal levels in the nocturnal mouse and the diurnal monkey. Combined with the observed differential expression of a PK2 signaling receptor in the retino-recipient brain targets of the ipRGC between the nocturnal mouse and the diurnal monkey, the mammalian diurnal/nocturnal determination likely lies among the retina-brain input pathways, upstream of the SCN clock.

Results

1. PK2 Signaling is Required for the Sustained Light-Induced Suppression of the Locomotor Activity and the Arousal in Mice.

Figure 1B:
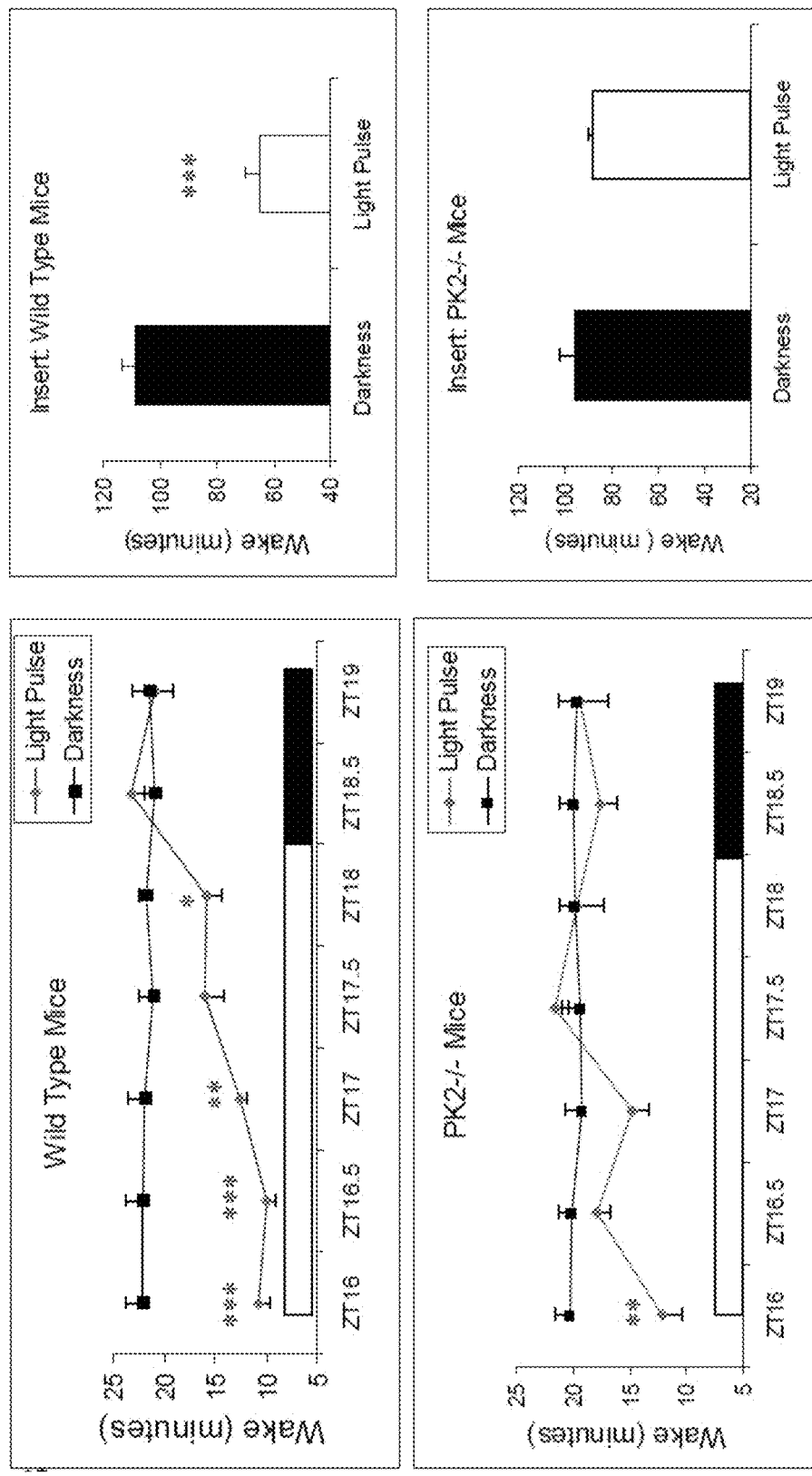

Mice deficient in genes of either PK2 (PK2−/−) or its receptor (PKR2) had reduced circadian rhythms of locomotor activity under constant darkness condition[29, 30]. We observed that the PK2−/− mice also displayed increased daytime locomotor activity under light/dark (LD) cycle, which is consistent with prior observation of increased wakefulness in the PK2−/− mice during light period[31]. These observations suggested that the light suppression effect is abnormal in the absence of PK2 signaling. We thus examined the suppression effect of light pulses on the locomotor activities and the arousal levels in the PK2−/− mice. When a light pulse (150 lux) was administrated to the wild type mice during the middle of dark period (ZT16-ZT18.5), the locomotor activities were significantly suppressed (FIG. 1A). In contrast, only marginal suppression of the locomotor activities by light pulses was observed for the PK2−/− mice (FIG. 1A and Insert). As expected, EEG/EMG recording revealed that light pulses suppressed wakefulness in the wild type mice (FIG. 1B and Insert). For the PK2−/− mice, the light suppression on the wakefulness was only significant for the first 30 min (FIG. 1B). Thus, light could still suppress the wakefulness in the PK2−/− mice, but the suppression effect was not be maintained.

Figure 2A:
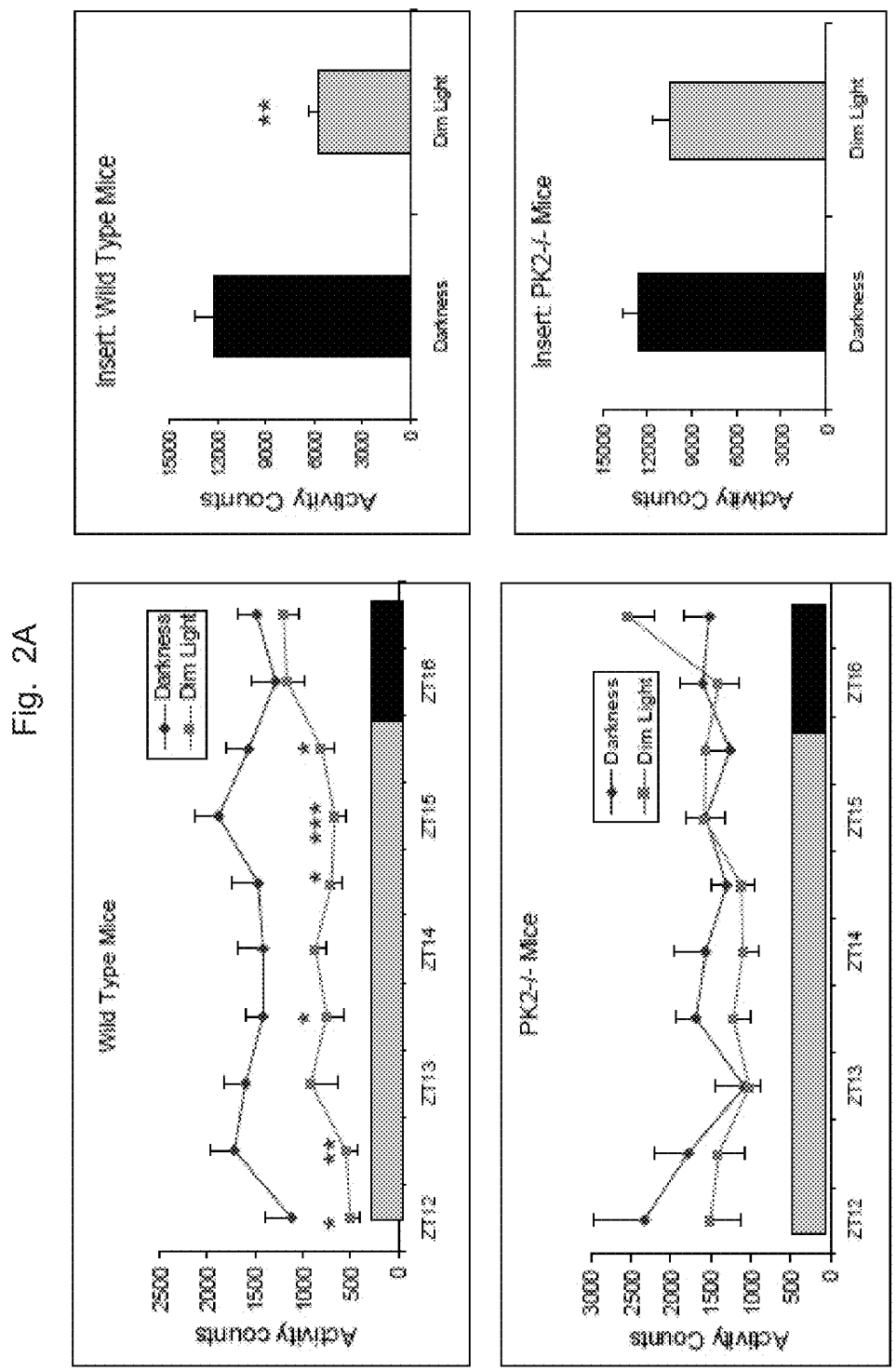
FIG. 2A-B graphically illustrates data from studies comparing activity counts and wakefulness time as a function of darkness and dim light exposure. For the PK2−/− mice, the wakefulness time under dim light and under darkness were quite similar, indicating only marginal arousal inhibition by the dim light in the absence of PK2 signaling, as described in detail in Example 1, below. For the wild type mice, the activity counts and the time staying awake during these four hours of dim light was much more reduced than under darkness, revealing a strong sleep induction effect of the dim light, as described in detail in Example 1, below.
Figure 2B:
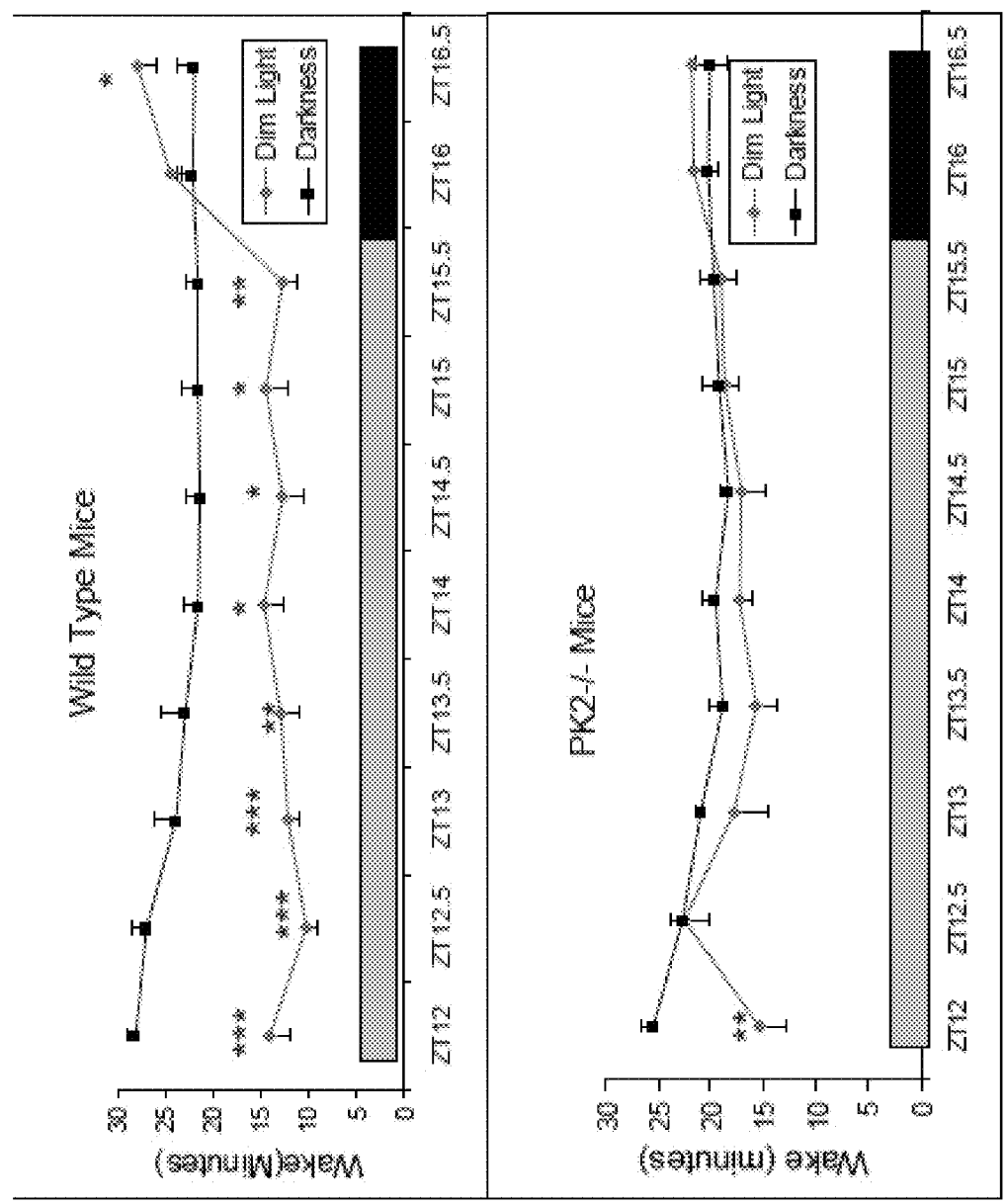

We further investigated the light suppression effect on the locomotor activities and the arousal levels with dim light. Just before the ending of the regular approximately 150 lux illumination condition at ZT12, the light intensity was dimmed to ~30 lux during the four-hour period corresponding to ZT12-ZT16. This reduced illumination continuously suppressed the locomotor activities of the wild type mice (FIG. 2A and Insert). In contrast, the PK2−/− mice displayed quite robust locomotor activities in response to the light intensity reduction, achieving the activity levels quite comparable to that were under darkness (FIG. 2A). This observation indicated that, at the high homeostatic drive for the activities during late day, dim light was no longer able to markedly suppress the locomotor activities in the PK2−/− mice. EEG/EMG recording confirmed the corresponding arousal levels affected by this dim light treatment. For the wild type mice, the time staying awake during these four hours of dim light was much more reduced than under darkness, revealing a strong sleep induction effect of the dim light (FIG. 2A). For the PK2−/− mice, the wakefulness time under dim light and under darkness were quite similar, indicating only marginal arousal inhibition by the dim light in the absence of PK2 signaling (FIG. 2B).

2. Expression of PK2 in the Intrinsically Photosensitive Retinal Ganglion Cells

Figure 3:
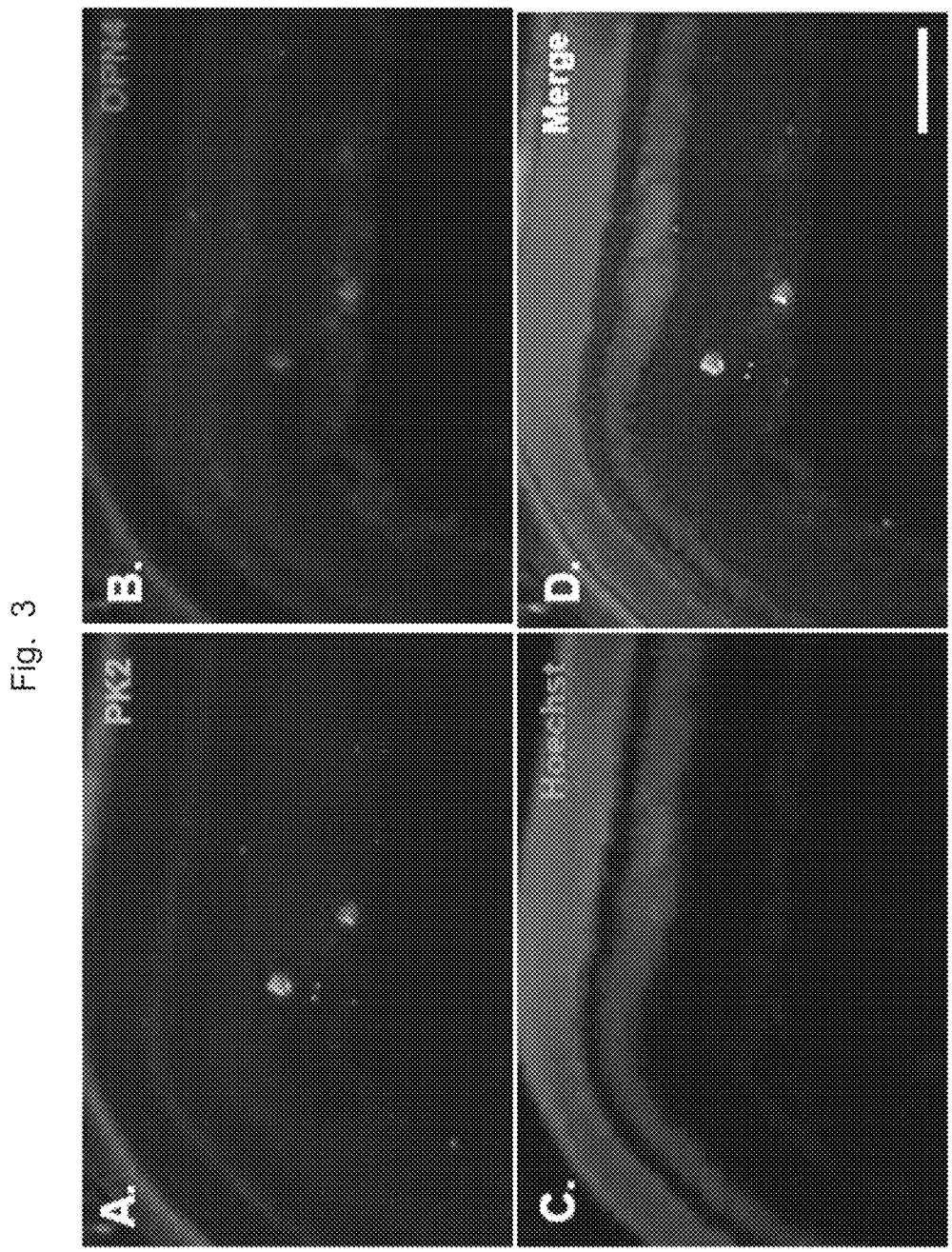
FIG. 3A-D illustrate images of retinal ganglion cells expressing PK2, where the expression of PK2 in the ipRGC was examined.

The diminished suppression effect of light on the arousal levels and the locomotor activities in the PK2−/− mice implicates that PK2 signaling is likely involved in ipRGC-brain neural pathways, as the ipRGC have been shown as the photic channels for the central transmission of the non-visional functions of light, including the locomotor activity suppression and sleep induction[22, 23, 24, 25, 32, 33]. We thus examined the likely expression of PK2 in the ipRGC. As shown in FIG. 3A and FIG. 7), PK2 is strongly expressed in some retinal ganglion cells. Further co-immunostaining studies indicated that all OPN4-positive retinal ganglion cells express PK2 (28/28 cells, FIG. 3). The approximately 100% co-expression of PK2 and OPN4 in the ipRGC indicated that PK2 of the ipRGC projects to the SCN and other non-visional light functional areas of brain, such as the superior colliculus[34, 35, 36].

3. Differential Expression of PK2 Receptor in the Brain Targets of the Intrinsically Photosensitive Retinal Ganglion Cells Between the Nocturnal Mouse and the Diurnal Monkey As with the nocturnal mouse, the PK2 expression was also detected in the retinal ganglion cells of the diurnal monkey (FIG. 4A). Also identical to that of the mouse, PK2 is co-expressed with OPN4 in the monkey ipRGC (FIG. 4B/D). Importantly, differential expression of PKR2, the brain PK2 receptor, in the SCN compartments was observed for the nocturnal mouse and the diurnal monkey. In the mouse brain, PKR2 is expressed in the entire SCN, covering both the ventral and dorsal compartments of the SCN (FIG. 5B)[6, 37]. It has been shown that ventral SCN is retinorecipient, i.e., receiving the retinal inputs for the light masking and circadian clock entrainment[9, 38]. The expression of PKR2 in the retinorecipient SCN in the mouse indicates that the mouse ventral SCN likely responds to PK2 signal from the ipRGC. Our previous electrophysiological studies have shown that PK2 increases the electric activities of neurons that express PKR2[39, 40]. In the monkey brain, PKR2 is only expressed in the dorsal SCN, but is not detected in the ventral SCN (FIG. 5A). As with the nocturnal animals, the ventral SCN has been shown as the retinorecipient compartment of the SCN clock[38, 41]. The absence of the PKR2 expression in the ventral SCN indicates an inability of the monkey SCN to respond to the PK2 signal from the ipRGC. Distinct expression of PKR2 between the mouse and monkey brains was also observed in the superior colliculus (SC), another important non-vision brain target of the ipRGC[34, 35, 36]. As shown in FIG. 5C, PKR2 was robustly expressed in the superficial layer of the SC in the monkey brain. The superficial layer of the SC is known to receive inputs from the retinal ganglion cells, including the ipRGC[34, 35, 36]. In contrast, PKR2 expression was not detected in the SC of the mouse brain (FIG. 5D), indicating the absence of PK2 signaling via the ipRGC-SC in the mouse.

Figure 6A:
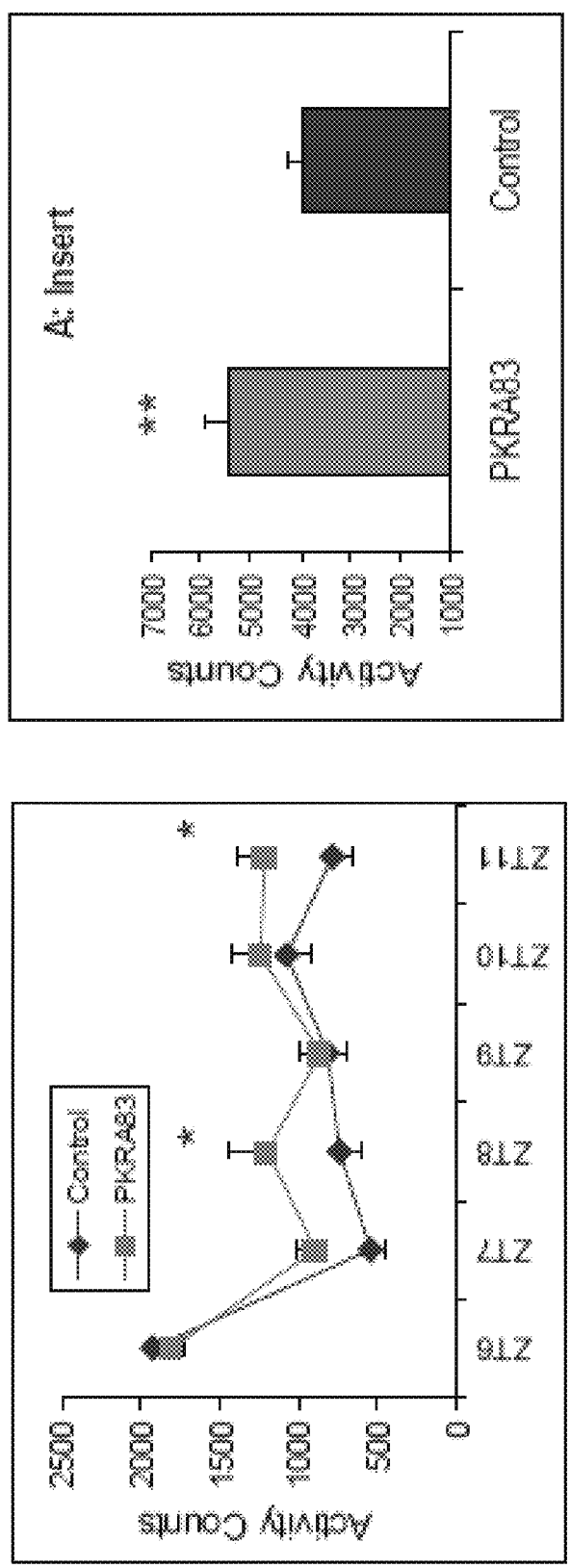
Figure 6C:
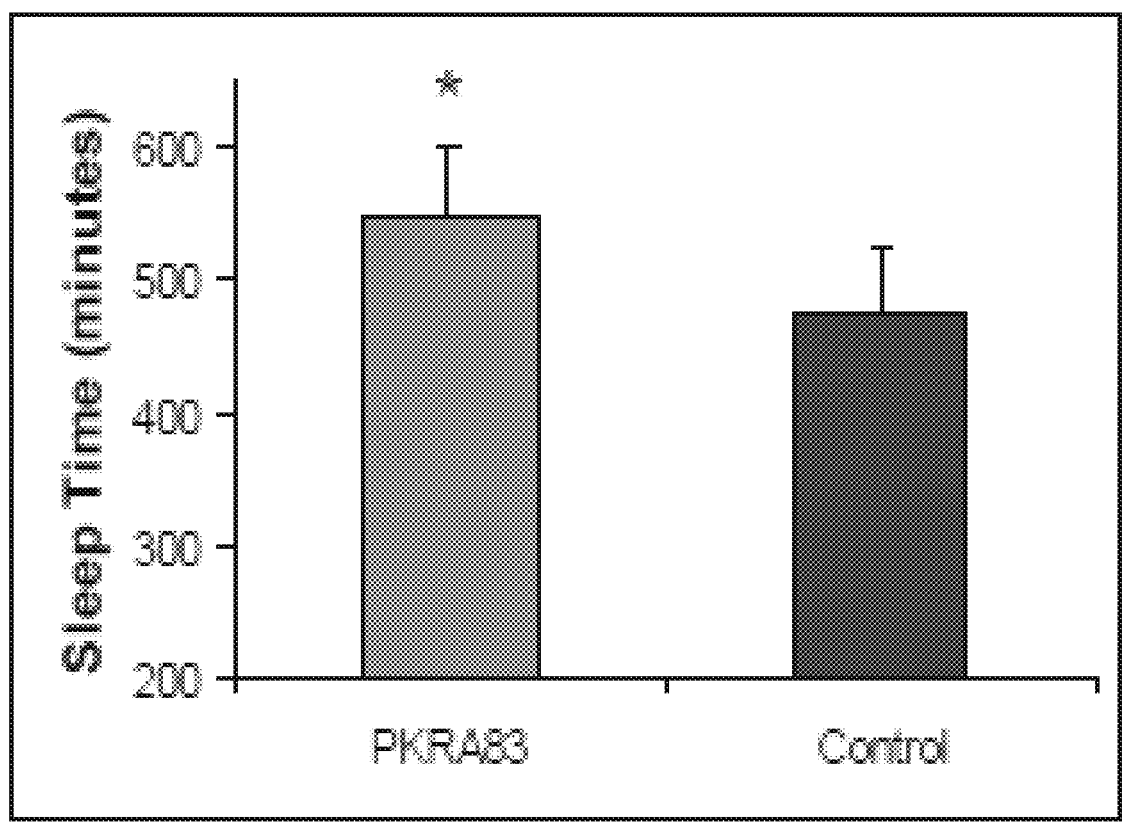

4. Opposite Effects of PK2 Blockade on the Arousal Levels in the Nocturnal Mouse and the Diurnal Monkey We next examined the effect of a synthetic PK2 antagonist, PKRA83, on the arousal levels in the mice and the monkeys. As shown in FIGS. 6A and 6B, administration of PKRA83 significantly increased the locomotor activity and the wakefulness in the mice. These results are consistent with prior observation of increased wakefulness in the PK2−/− mice[31]. Thus, PK2 signal is overall inhibitory for the arousal levels for the nocturnal mice. In contrast, administration of the PK2 antagonist in the monkeys resulted in a significant increase (>70 minutes) of the sleep time (FIG. 6C), indicating that the PK2 signal is stimulatory for the arousal level in the diurnal monkeys.

CONCLUSIONS

Figure 8:
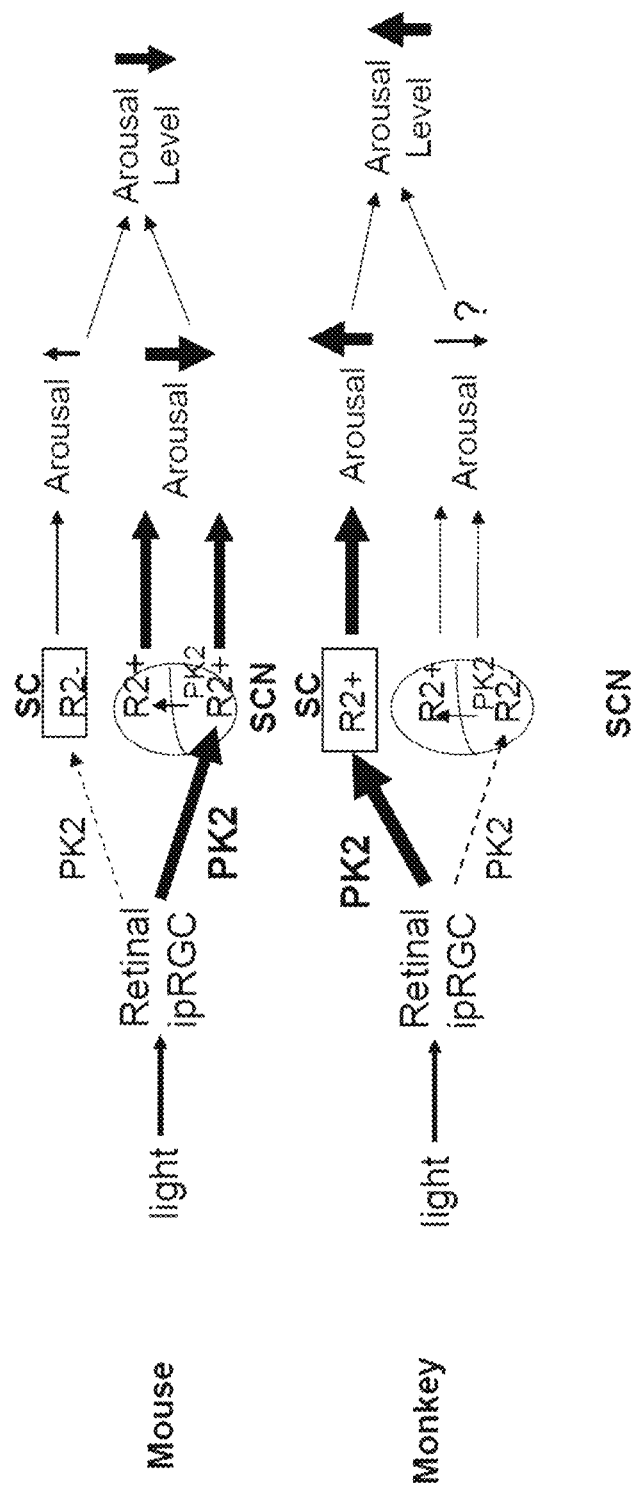
FIG. 8 illustrates a diagram showing the differential arousal regulation by the PK2 signaling of ipRGC onto brain targets, as described in detail in Example 1, below.

We have shown that PK2 is expressed in the centrally projecting ipRGC. As the ipRGC are the only photic channels for the central transmission of the non-visual functions of light, the absence of the sustained light-induced activity suppression and sleep induction in the PK2−/− mice indicates that the PK2 signaling of the ipRGC is critical for transmitting the effect of light on the arousal regulation in the nocturnal mouse. Blocking the PK2 signaling via administration of a PK2 antagonist demonstrated the opposite effects of the PK2 signal on the arousal levels: being inhibitory for the nocturnal mouse and stimulatory for the diurnal monkey. Taken together, these results demonstrate that a mechanism of the nocturnal and diurnal divergence lies in the differential PK2 signaling of the ipRGC onto their brain targets (FIG. 8).

The PK2 signaling of the ipRGC likely regulates the arousal levels via impinging on the brain targets of the ipRGC, particularly the SCN and the SC. The differential expression of the PK2 receptor (PKR2) in the retino-recipient compartment of the SCN and the retinorecipient superficial layer of the SC may then underlie the opposite effects of light on the arousal levels between the nocturnal mouse and the diurnal monkey. In the mouse brain, PKR2 is robustly expressed in the retinorecipient SCN, but absent in the SC, and the PK2 signaling of the ipRGC thus funnels through arousal-inhibitory ipRGC-SCN pathway in the nocturnal mouse. In contrast, PKR2 is not expressed in the retinorecipient ventral SCN of the monkey brain, but strongly expressed in the retinorecipient superficial layer of the SC, and thus the ipRGC-SC pathway dominates in the diurnal monkey.

The PK2 signaling of the ipRGC-SC pathway is likely to be stimulatory for the arousal levels. SC has previously been indicated as a critical nucleus for the light-induced arousal or other higher brain functions, such as attention, that are closely tied with increased arousal[42, 43, 44, 45]. SC may mediate the light-driven arousal via the ascending projections to cortices that are routed through the lateral posterior/Pulvinar complex of the thalamus[46, 47]. Alternatively, SC may promote arousal via the descending projections to the mesencephalic reticular formation, an important component of the ascending activation system[42, 43, 44, 45]. In the monkeys, bilateral lesions of the SC have been found to drastically affect the arousal levels, including response to light[42]. Lesion studies in rats have revealed that the SC is important for EEG desynchronization (arousal) in response to light flashes[43]. This rat lesion study suggests that the ipRGC-SC pathway may be stimulatory for the arousal levels for the nocturnal animals, at least briefly in response to light flashes. Overall, light is inhibitory for the arousal levels of the nocturnal animals as the inhibitory ipRGC-SCN pathway dominates. It is well known that, compared to the nocturnal animals, the overall size of the SC, the lateral posterior/Pulvinar complex of the thalamus, and the associated cortices are all significantly enlarged and expanded in the diurnal mammalian species, such as the primates[48, 49]. As the mammalian species are believed to start being nocturnal[50], diurnality of the mammals may evolve via the enhancement of the arousal-stimulatory retina-SC pathway and the simultaneous diminishment of the arousal-inhibitory retina-SCN pathway. This model indicates that the nocturnal/diurnal determination lies in the upstream of the SCN circadian clock, and thus divergent signaling downstream of the SCN clock may not be necessary.

Methods

Animals:

PK2−/− mice and their littermate wild type controls in mixed genetic background were generated as described[29, 31]. Mice were fed at libo and housed at regular light/dark cycle, with lights (approximately 150 lux white light) on at 7:00 a.m. (Zeitgeber Time ZT0, light period ZT0-ZT12) and lights off at 7:00 p.m. (ZT12, dark period ZT12-ZT0). All animal procedures were approved by appropriate institutional animal use committee.

Measurement and Analysis of the Locomotor Activity in Mice:

Monitoring of the locomotor activity was carried out as described[29]. Briefly, mice were individually housed with cages equipped with infrared beams for the monitoring of the locomotor activity (AccuScan Instrument Inc. Columbus, Ohio). Mice were housed at regular 12 h Light (approximately 150 lux white light): 12 h Dark cycle. The locomotor activities were recorded as counts per 10-min interval and were analyzed in 30 or 60 min pins. Light pulses or dim light at the indicated intensities were administered.

Measurement and Analysis of the Arousal Level in Mice:

Electrodes for recording the electroencephalographic (EEG) and electromyogram (EMG) signals were implanted as described[29, 31]. The mice were connected to a swivel system of tether/commutator system (Plastics One, Roanoke, Va.) for the collection of the EEG/EMG signals. The EEG/EMG signals were amplified using a Grass Model 78™ (Grass Instruments, West Warwick, R.I.) and filtered (EEG: 0.3-100 Hz, EMG: 30-300 Hz) before being digitized at a sampling rate of 128 Hz, stored on a computer. After sleep data were collected, EEG/EMG records were scored with SleepSign™ software sleep scoring system (Kissei Comtec America, Irvine, Calif.) as described[31]. Mice were housed at a regular 12 hour (hr) light/12 hour dark cycle. Light pulses or dim light at the indicated intensities were administered.

In Situ Hybridization:

Procedures for In situ hybridization were carried out similarly as described[6, 7]. Tissue sections were cut at −20° C., and then fixed with 4% paraformaldehyde, followed by three washes of 0.1M phosphate buffer, air-dried, and stored at −20° C. until use. For In situ hybridization, sections were dried at room temperature, followed by pretreatment of proteinase K (1 µg/ml). Sections were then air-dried and hybridized with $S^{35}$-labelled riboprobes by incubation at 60° C. for 18 hours. After hybridization, tissue sections were treated with RNase (20 µg/ml) (Sigma-Aldrich, St. Louis, Mo.), decreasing salinity washes and high stringency (68° C.) wash. After dehydration and air-drying, tissue sections were exposed to Kodak Biomax™ film. Images were captured with image analysis system (MCID, Imaging Research, Ontario, Canada).

Immunohistochemistry:

Immunohistochemistry was performed according to previous publications[51, 52]. Retinal sections were mounted onto coated glass slides. Sections were rehydrated in PBS for 20 minutes then immersed in a blocking buffer containing 2% BSA, 0.5% Tween-20 and 0.05% Triton-X 100 for 1 hour. Primary antibody for PK2 (Hamster monoclonal, 1:200, Roche Inc.) or OPN4 (Affinity purified rabbit polyclonal, 1:200, Millipore Inc.) was added to the sections overnight at 4° C. Slides were washed with PBS containing 0.5% Tween-20 five times for 5 minutes each. Anti-rabbit or anti-hamster secondary antibodies (Alexa Fluor 488 or 555 1:2000; Invitrogen Inc.) were then applied, followed by incubation with 10 µg/ml Hoechst 33342™ (Invitrogen Inc) for 5 minutes at room temperature to stain the nucleus. Sections were viewed under a Nikon inverted fluorescence microscope (Model TE-2000U™; Nikon Inc, Tokyo, Japan). Images were captured with a SPOT digital camera (Diagnostic Instruments, Inc, Sterling Heights, Mich.). For DAB (3,3'-diaminobenzidine) immunostaining, sections were incubated with anti-PK2 antibody (Hamster monoclonal, 1:500 dilution) antibody, followed by incubation with biotinylated anti-hamster secondary antibody. Color development of DAB immunostaining was carried out with the standard ABC method[52].

Pharmacological Experiments of Examining the Effect of a PK2 Antagonist on the Activity or Arousal Levels in the Mice and the Monkeys:

A PK2 antagonist (PKRA83) was prepared similarly as described[53]. PKRA83 (40 mg/kg) was administered to the mice intraperitoneally at ZT6. PKRA83 (10 mg/kg) was administered to the monkeys intramuscularly at ZT10. For the pharmacological experiments, animals were treated with either the vehicle or antagonist and then crossed over with the opposite treatments one week later to form paired controls.

Sleep and activity data of the PK2 antagonist or control-treated mice were acquired and analyzed as described for the PK2−/− mice. For the sleep studies of the monkeys, young adult monkeys (*Macaca fascicularis*) were housed under standard light (white light ~250 lux) and dark cycle. The measurement and analysis of the arousal levels in the monkey were carried out as follows. A wearable wireless sleep tracker, similar to one described previously for human subjects[54,55,56,57] and for non-human primates[58], was used. This wireless system enabled remote monitoring of the sleep/wake status of the monkeys for an ambulatory setting for a long time with minimal disturbing of the monkeys. The sleep data obtained from the wireless sleep tracker were verified with concurrent recording of infrared video camera. The sleep data of the sleep trackers were retrieved daily with mobile phones that were seated about ten meters away from the animal cages, without physical contact with the monkeys. Previous studies have shown excellent agreement of sleep data obtained by the sleep tracker, video camera and classical sleep/wake data obtained by the EEG/EMG method[54, 57, 59].

Statistics:

To reduce the impact of data variations due to ultradian rhythms, the measurements of mouse locomotor activity and EEG/EMG were performed two times, and the average values of these two measurements were used in statistical analyses. Statistical analyses were performed with one or two ways ANOVA by using GraphPad Prism Software Version 5.0™ (San Diego, Calif.), followed by appropriate post-tests.

FIGURE LEGENDS

FIG. 1A. The effects of light pulses on the locomotor activities and the arousal levels. The white bar shows the light pulses (150 lux) administered to WT (N=6) and PK2−/− mice (N=7) during ZT16-ZT18.5 (2.5 hrs). The analysis bin sizes were 30 min, with values being means±sem. A. Light pulses significantly inhibited the locomotor activity in the WT mice (P<0.01, Two-way ANOVA, *, P<0.05, **, P<0.01 by Bonferroni's post hoc test). The effect of light pulses on the locomotor activity of the PK2−/− mice was not significant (P>0.05, Two-way ANOVA). The insert shows the locomotor activity in the entire 2.5 hrs (*, P<0.05, paired t-test).

FIG. 1B. Light pulses significantly deceased the wake time in the WT mice (P<0.0001, Two-way ANOVA, *, P<0.05, , P<0.01, *, P<0.001 by Bonferroni's post hoc test). The inhibitory effect of light pulses on the arousal levels of the PK2−/− mice was only significant for the first 30 min (P<0.05, Two-way ANOVA, , P<0.01, by Bonferroni's post hoc test). The insert shows the wake minutes of the entire 2.5 hrs (*, P<0.001, paired t-test). The inhibitory effect of light pulse on the arousal levels in the entire 2.5 hrs was not significant for the PK2−/− mice (P>0.05, paired t-test).

FIG. 2A. The effects of dim light on the locomotor activities and the arousal levels. The grey bar shows the four hours of dim light (30 lux) that was administered during ZT12-ZT16 to the WT (N=6) and the PK2−/− mice (N=7). A. Compared to darkness, dim light significantly decreased the locomotor activity in the WT mice (P<0.0001, Two-way ANOVA, *, P<0.05, , P<0.01, *, P<0.001 by Bonferroni's post hoc test). The inhibitory effect of dim light on the locomotor activity was not significant for the PK2−/− mice (P>0.05, Two-way ANOVA). The inserts show the locomotor activities in the entire four hours (**, P<0.01, paired t-test).

FIG. 2B. Compared to darkness, dim light significantly decreased the arousal levels in the WT mice (P<0.0001, Two-way ANOVA, *, P<0.05, , P<0.01, *, P<0.001, by Bonferroni's post hoc test). The inhibitory effect of dim light on the arousal levels of the PK2−/− mice was only significant for the first 30 min (P<0.05, Two-way ANOVA, **, P<0.01, by Bonferroni's post hoc test).

FIG. 3. Coexpression of PK2 and OPN4 in retinal ganglion cells of the mouse retina. The PK2 immunostaining is shown as green (A) whereas the OPN4 fluorescent immunolabeling is shown in red (B). The nuclear counterstaining is shown as blue (C). Coexpression of PK2 and OPN4 in the retinal ganglion cells is apparent (D). Two cells strongly immunostained by PK2 and OPN4 are shown. Scale bar, 40 µm.

Figure 4:
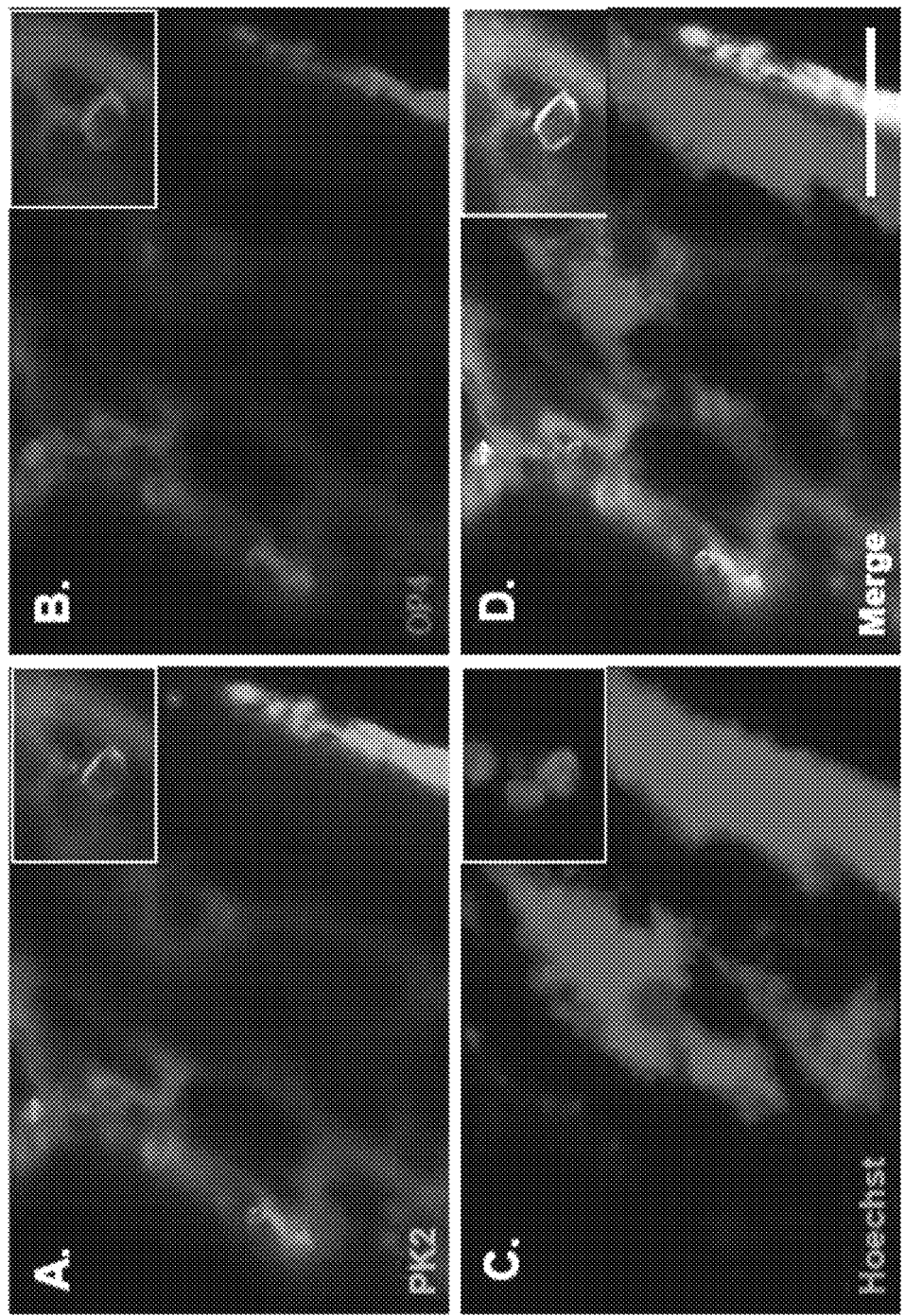
FIG. 4A-D illustrates images of retinal ganglion cells of the diurnal monkey.

FIG. 4. Coexpression of PK2 and OPN4 in retinal ganglion cells of the monkey retina. The PK2 immunolabeling is shown as green (A) whereas the OPN4 fluorescent immunolabeling is shown as red (B). The nuclear counterstaining is shown as blue (C). Co-expression of PK2 and OPN4 in the retinal ganglion cells is apparent (D). Inserts show the higher magnification images of a representative positive cell. Scale bar, 20 µm.

Figure 5:
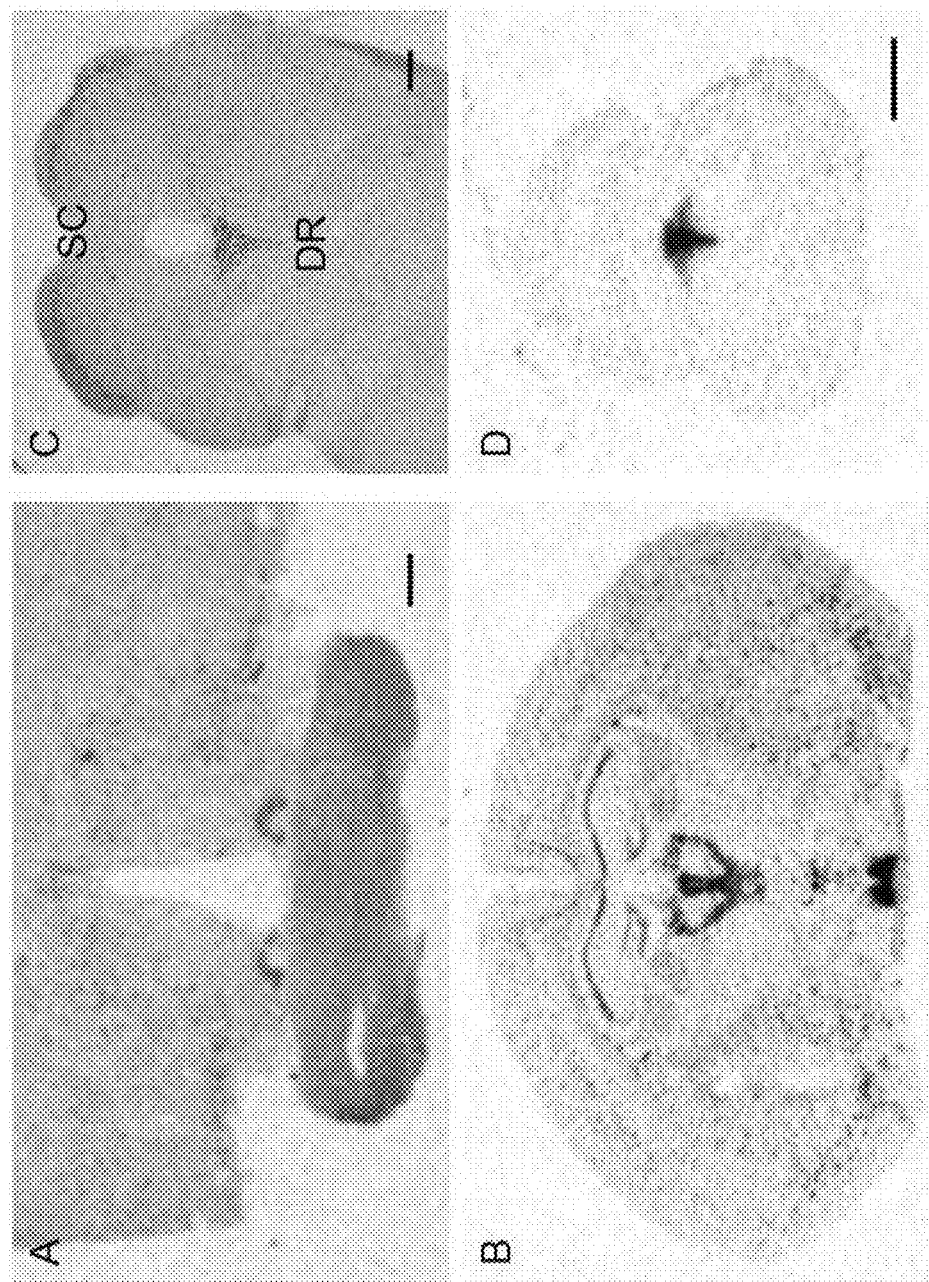
FIG. 5A-D illustrates images of PKR2 expression in mouse brain and monkey brain.

FIG. 5. Differential expression of PKR2 mRNA in retinorecipient targets of the mouse and the monkey brains. A. Detection of PKR2 mRNA in the dorsal compartment of suprachiasmatic nucleus (SCN), but not in the ventral SCN, of the monkey brain. B. Detection of PKR2 mRNA in the entire SCN, both the ventral and dorsal compartments, in the mouse brain. C. Detection of PKR2 mRNA in the superficial layer of the superior colliculus (SC) of the monkey brain. D. Absence of PKR2 mRNA in the SC of the mouse brain. Note the expression of PKR2 in the dorsal raphe nucleus (DR) in both the mouse and monkey brains. Scale bar, 1 mm.

FIG. 6. Differential effect of a PK2 antagonist PKRA83 on the locomotor activity and arousal levels in mice and monkeys. A. PKRA83 significantly increased the locomotor activity of the mice (N=16, P<0.05, Two-way ANOVA, *, P<0.05, by Bonferroni's post hoc test). B. PKRA83 significantly increased the wake time of the mice (N=6, Two-way ANOVA, *, P<0.05, by Bonferroni's post hoc test). The inserts of A and B show the PKRA83 increased the locomotor activity and the wake minutes during the six hours day time period, respectively (**, P<0.01, paired t-test). C. PKRA83 significantly increased the sleep time of the monkeys (N=9, *, P<0.05, paired t-test).

FIG. 7. Expression of PK2 in the retinal ganglion cells of the mouse retina. PK2 immunolabeling was developed by DAB (3,3'-diaminobenzidine). A. Examples of two PK2-positive retinal ganglion cells, one nondisplaced and one displaced, are marked with arrows. B. PK2 DAB immunostaining with hematoxylin counterstaining. Examples of two PK2-positive retinal ganglion cells, one strongly and one more modestly stained, are marked with arrows. Scale bar, 20 µm.

FIG. 8. Diagram showing the differential arousal regulation by the PK2 signaling of ipRGC onto brain targets. PK2 is expressed in the ipRGC, the only photic channels that transmit central non-vision functions of light. Overall, the PK2 signaling is stimulatory for the diurnal monkey and inhibitory for the nocturnal mouse, as shown by the antagonist blockade and PK2-deficiency. The differential expression of PKR2 in the retinorecipient ventral SCN and the superficial layer of SC indicates that the PK2 signaling of the ipRGC funnels through ipRGC-SCN and ipRGC-SC for the mouse and the monkey, respectively. For the nocturnal animals, the arousal stimulation via the ipRGC-SC pathway by light is minor (transient, not sustained), consistent with the absence of PKR2 in the SC of the mouse brain. The PK2 signaling of the ipRGCSCN pathway is clearly inhibitory for the nocturnal mouse, although it is unclear whether it is inhibitory or stimulatory for the diurnal animals. In fact, although the supporting evidence for the SCN as the master circadian clock is overwhelmingly strong for the nocturnal mammals, such claim has actually limited supporting evidence in the case of the diurnal animals. The well cited work of increased sleep by SCN lesion in squirrel monkeys, interpreted as the arousal-promoting of the SCN for the diurnal animals, could be explained by concurrent lesions to the retinohypothalamic tract. Our model indicates that the mammalian diurnal/nocturnal determination is mediated by the differential signaling of the ipRGC onto their brain targets, and thus divergent signaling mechanisms downstream of the SCN may not be necessary.

Example 2: PK2 Functions as a Signal Molecule for the ipRGC to Brain Connection

This example describes studies showing that PK2 functions as an output molecule for the circadian clocks in the ipRGC to regulate wakefulness and sleep for the mammals, and that PK2 antagonists induce or promote sleep.

The circadian clocks in the retina have largely been thought to regulate local physiology and function such as electroretinogram amplitude and phagocytosis of photoreceptor outer segment disks. Our findings revealed that PK2 functions as an output molecule for the circadian clocks in the ipRGC to regulate wakefulness and sleep for the mammals.

Figure 9:
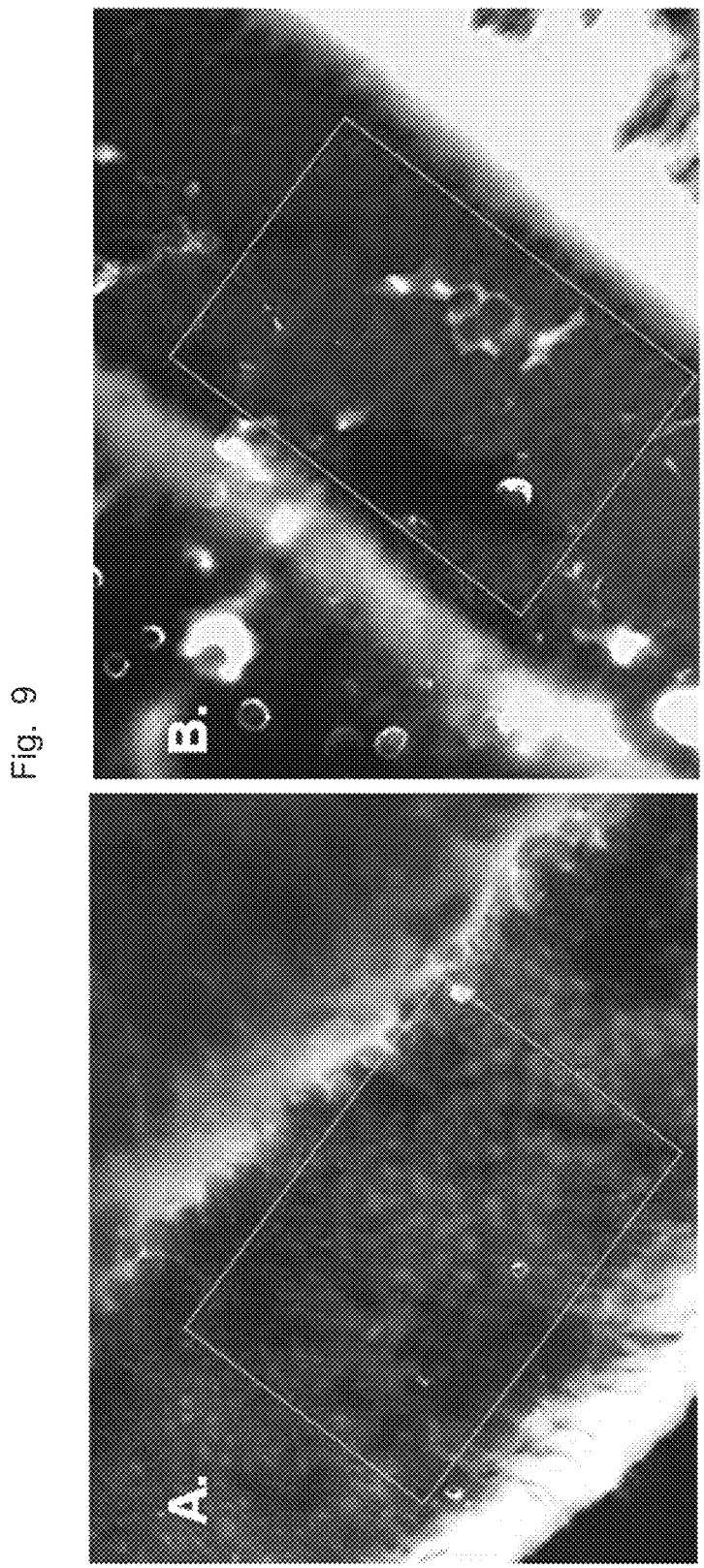
FIG. 9A-B illustrates images showing PK2 expression in the outer nuclear layer of retina was found to be increased during continuous darkness, where the images show up-regulation of PK2 in the outer nuclear layer of retina at CT4 (FIG. 9B) compared to ZT4 (FIG. 9A), the PK2 immunostaining is shown; the boxed areas indicate the outer segment of mouse retina; the nuclear counterstaining is shown as blue, as described in detail in Example 1, below.

PK2 expression in the outer nuclear layer of retina was found to be increased during continuous darkness. As shown in FIG. 9, expression of PK2 in the outer nuclear layer of the retina is much higher at CT4 than at ZT4. Cell counting revealed that at ZT4, the percentage of photoreceptors that were PK2-positive was approximately 0.1%. ACT4, the percentage of PK2-positive photoreceptors was increased to approximately 2%, indicating that the PK2-positive cells are likely cones. FIG. 9 illustrates images showing up-regulation of PK2 in the outer nuclear layer of retina at CT4 (panel B) compared to ZT4 (panel A): in FIG. 9, illustrated is upregulation of PK2 in the outer nuclear layer of retina at CT4 (panel B) compared to ZT4 (panel A); the PK2 immunostaining is shown; the boxed areas indicate the outer segment of mouse retina; the nuclear counterstaining is shown as blue; the upregulation of PK2 at CT423 (panel B), compared to ZT4 (panel A), is apparent. The upregulation of PK2 in the outer nuclear layer of the mammalian retina may be linked to increased neural activity of photoreceptors during darkness.

Figure 10:
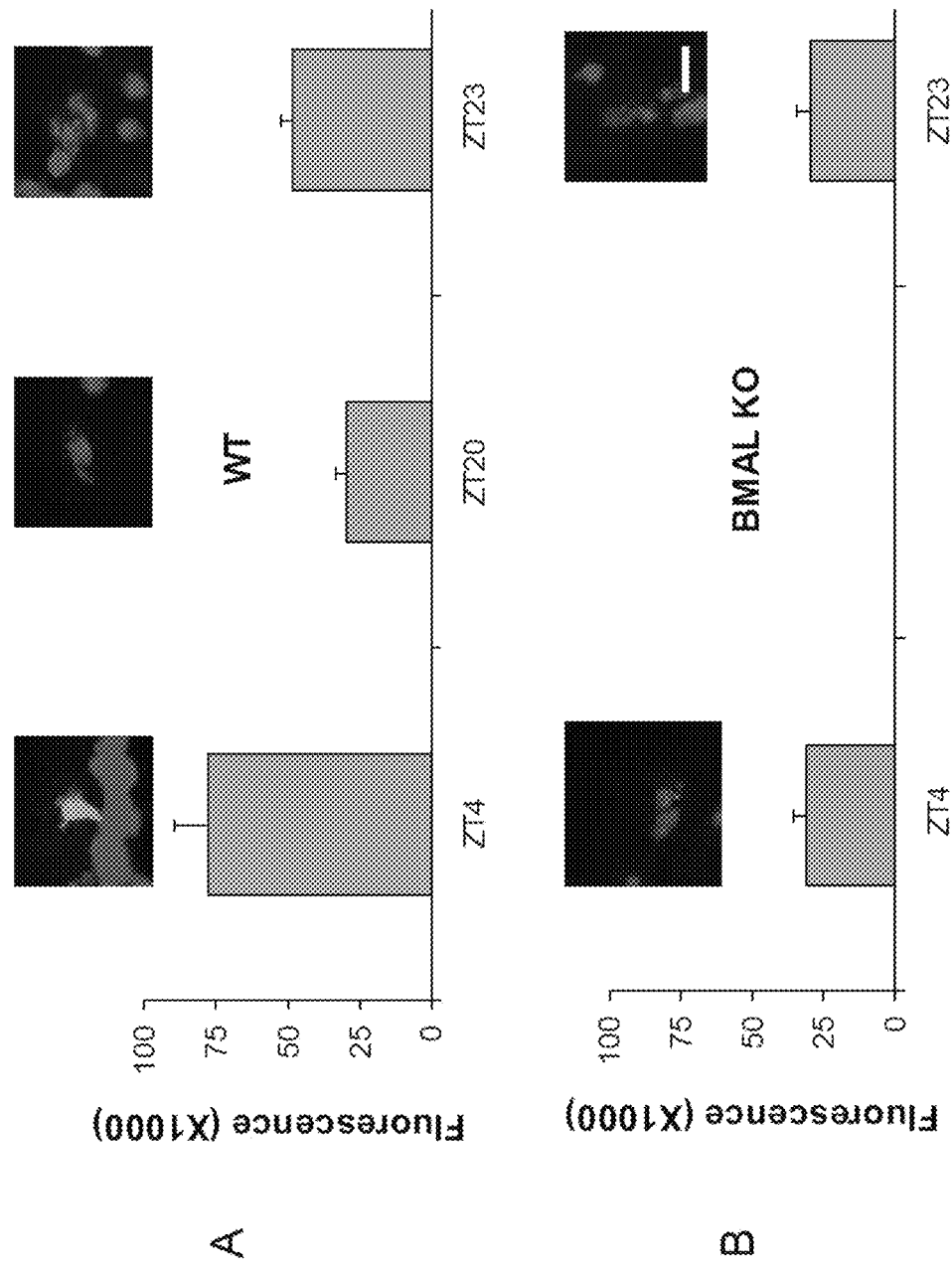
FIG. 10A-B graphically illustrates the clock-dependent oscillatory expression of PK2 in the ipRGC.

The PK2 expression in the ipRGC was further shown to oscillate in a Bmal1-dependent manner under light and dark conditions (FIG. 10). In wild type mice, the peak and trough PK2 levels in the ipRGC were around ZT4 and ZT20, respectively. In contrast, PK2 levels in the ipRGC of Bmal1-deficient mice were constantly low, and no apparent PK2 oscillation was observed. The oscillatory phase of PK2 levels in the ipRGC, including the peak and trough timing at approximately ZT4 and approximately ZT20, respectively, is quite similar to the PK2 oscillation observed in the SCN clock, indicating the regulation by same molecular oscillators. Together, these results indicate that the oscillatory expression of PK2 in the ipRGC is a clock-dependent process.

Figure 11:
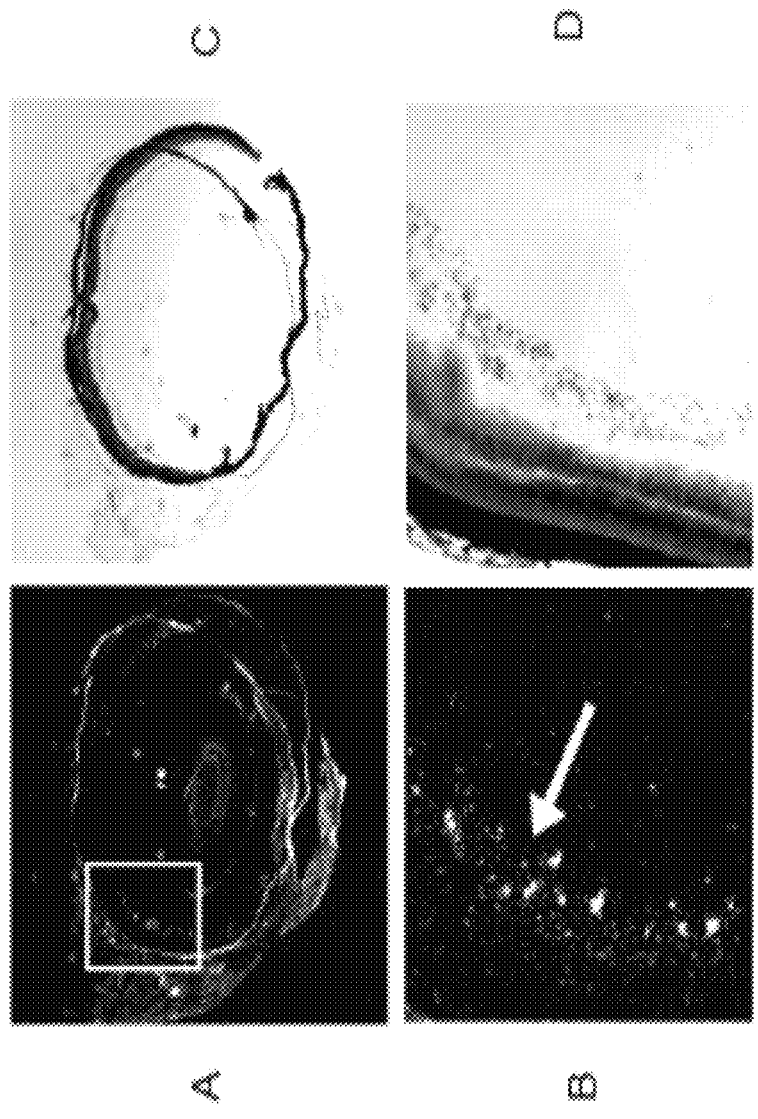
FIG. 11A-D illustrate images of in situ hybridization showing that PKR2, a PK2 receptor, is expressed in certain retinal ganglion cells.

In situ hybridization shows that PKR2, a PK2 receptor, is expressed in certain retinal ganglion cells (FIG. 11). PKR2 expression is only detected in the retinal ganglion cells, but not in the bipolar cells. The abundance and diameter features of these PKR2-positive cells in the layer of retinal ganglion cells indicate that these PKR2-positive cells are the ipRGC. FIG. 11 illustrates images showing PKR2 expression in certain retinal ganglion cells; in FIG. 11, illustrated is PKR2 expression in certain retinal ganglion cells; PKR2 mRNA is detected by in situ hybridization; Panel A shows the PKR2 signals in the retinal ganglion cell layer; the higher magnification image of boxed area is shown in Panel B; in panel B, individual retinal ganglion cells that are PKR2-positive are apparent; Panels C and D show the Nissl staining of eye sections, corresponding to panel A and B, respectively.

Figure 12:
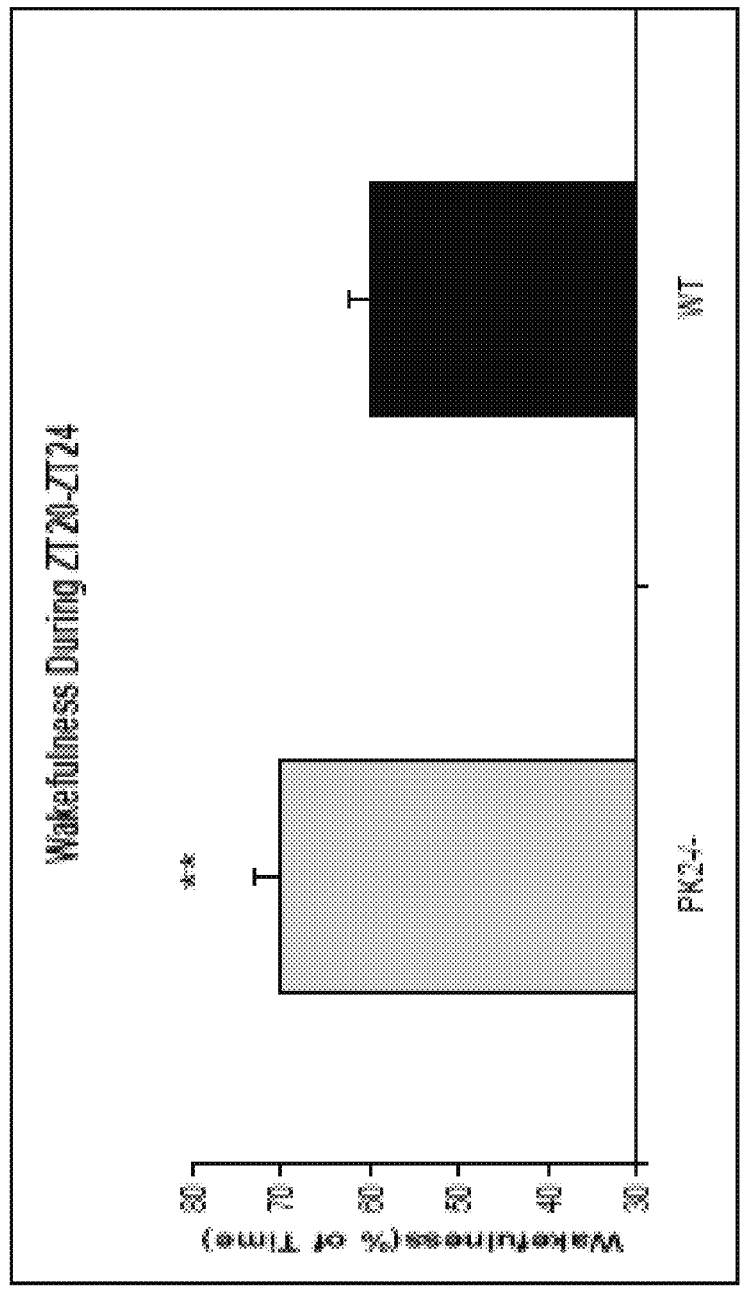
FIG. 12 graphically illustrates data showing that the arousal level was increased in the PK2-deficient (PK2−/−) mice during late night, it shows increased wakefulness in the PK2−/− mice during late night period (ZT20-ZT24), as described in detail in Example 2, below.

As shown in FIG. 12, the arousal level was increased in the PK2-deficient (PK2−/−) mice during late night, particularly between ZT20-ZT24 (the four-hour period before the light on). Thus, the PK2 signal inhibits the arousal levels in the mice during this period. FIG. 12 graphically illustrates data showing increased wakefulness in the PK2−/− mice during late night period (ZT20-ZT24).

Figure 13:
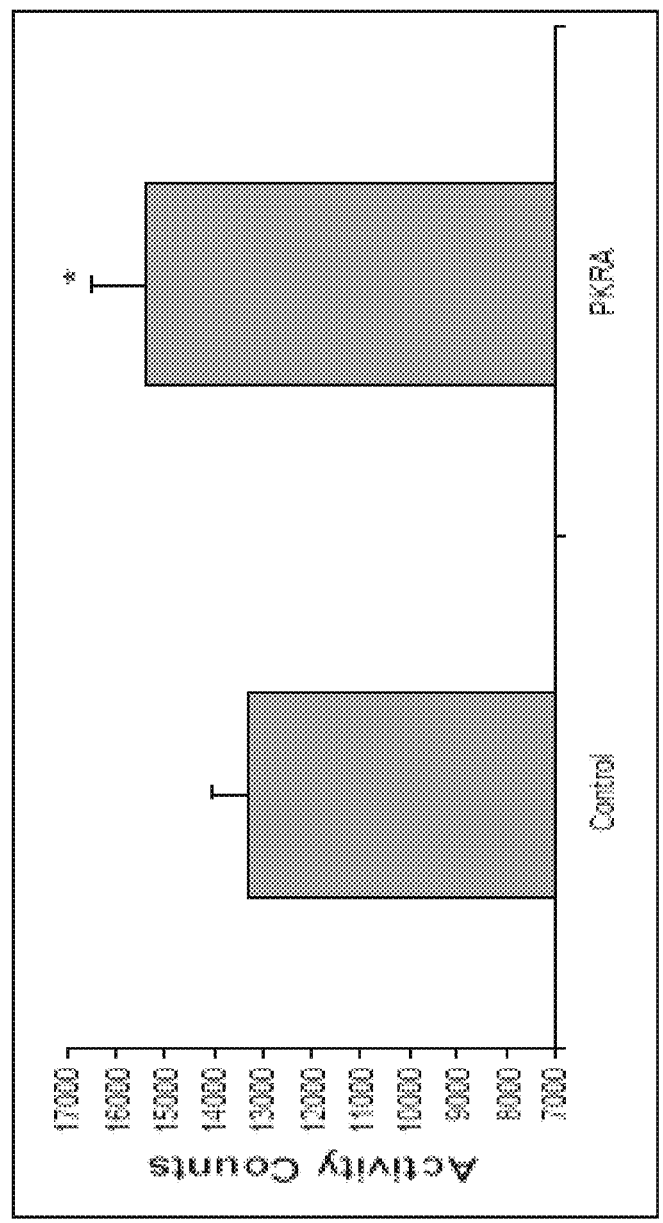
FIG. 13 graphically illustrates data showing that the ocular topic delivery of PK2 antagonist (PKRA) increased the locomotor activity of the PKRA-administered mice as compared to control mice (no antagonist given), as described in detail in Example 2, below.

The effect of a PK2 antagonist on the locomotor activity was tested in wild type mice. As shown in FIG. 13, PK2 antagonist delivered during the late night via ocular topic application increased the locomotor activity, and thus wakefulness level in the mice. FIG. 13 graphically illustrates data showing ocular topic delivery of PK2 antagonist increased the locomotor activity of the mice.

Figure 14:
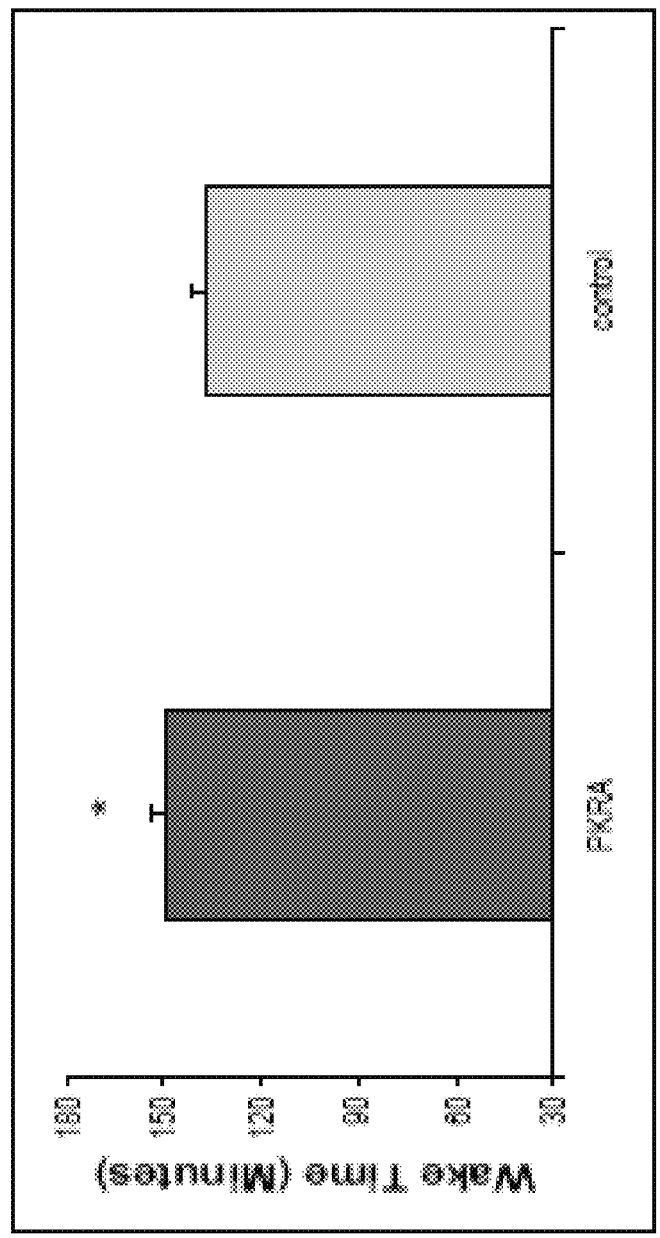
FIG. 14 graphically illustrates data showing the effect of a PK2 antagonist (PKRA) on the arousal level of mice as compared to control mice (no antagonist given), as described in detail in Example 2, below.

FIG. 14 graphically illustrates data showing the effect of a PK2 antagonist (PKRA) on the arousal level of mice: ocular topic application of PK2 antagonist at day time significantly increased the wake time of the mice (*, $P<0.05$, paired t-test).

As the effect of PK2 signaling on the arousal levels is reversed in diurnal mammals, compared to nocturnal mammals, the PK2 signaling is to stimulate wakefulness in diurnal subjects such as monkeys or human beings. As PK2 antagonist is shown to increase wakefulness in the mice (FIG. 14), the same PK2 antagonist is expected to inhibit wakefulness, i.e., to promote sleep in diurnal subjects such as monkeys. FIG. 14 graphically illustrates the effect of a PK2 antagonist ((3R)-1-(4-Fluoro-3-methoxybenzyl)-N-(9-chloro-3,4-dihydro-2H-1,5-benzodioxepin-7-ylmethyl)-N-isobutylpyrrolidine-3-carb oxamide, the so-called "PKRA83") on the arousal level of mice. Ocular topic application of PK2 antagonist significantly increased the wake time of the mice (*, $P<0.05$, paired t-test).

Figure 15:
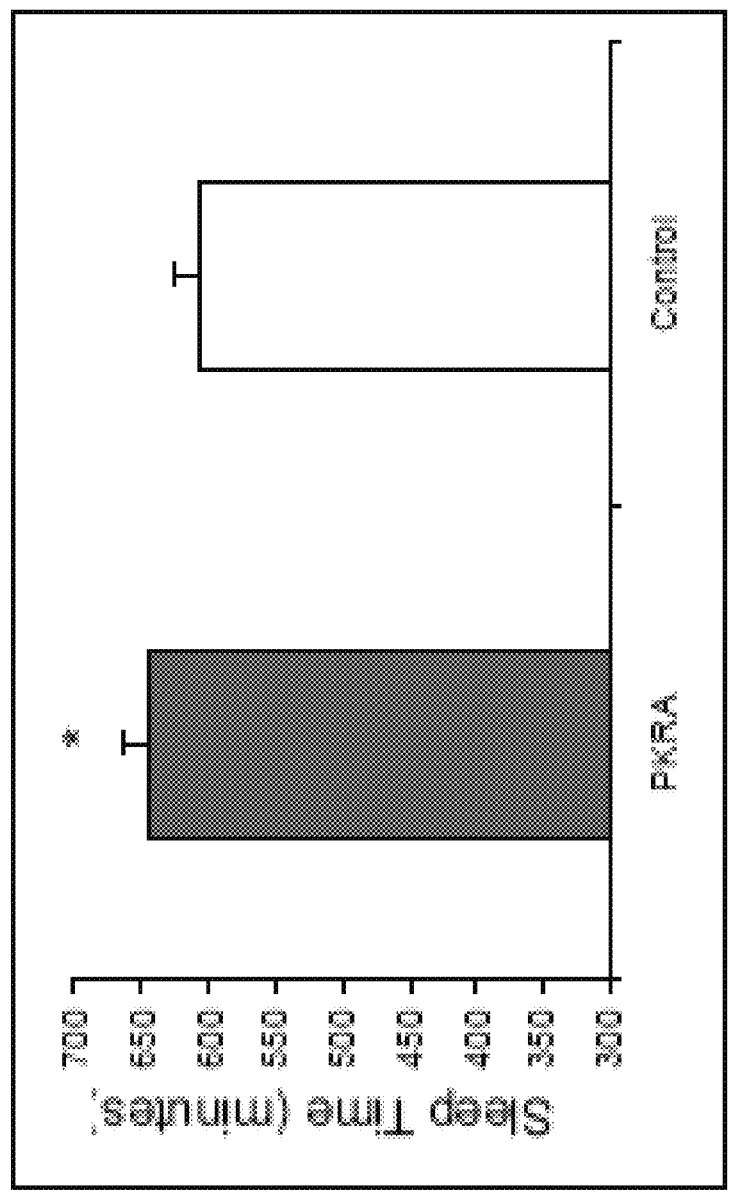
FIG. 15 graphically illustrates data showing the effect of a PK2 antagonist (PKRA83) on the sleep of monkeys, as compared to control (no antagonist given), as described in detail in Example 2, below.

We tested the effect of a PK2 antagonist on the arousal levels in monkeys via ocular topic delivery. As shown in FIG. 15, topic application of PK2 antagonist promotes sleep in monkeys. FIG. 15 graphically illustrates data showing the effect of a PK2 antagonist (PKRA83) on the sleep of monkeys. Ocular topic application of PK2 antagonist significantly increased the sleep time of the monkey (*, $P<0.05$, paired t-test).

As the ipRGC express PKR2 and also express PK2 from late night and the entire day time period, PK2 is also likely released from the dendrites or collateral axons of ipRGC to activate the PKR2 receptors on the neighboring ipRGC, i.e., PK2 couples the neural activity of ipRGC. Thus, as provided herein, methods that block PK2 signaling in the retina will be sleep-promoting for disease conditions such as advanced sleep phase disorder, which are expected to have advanced phase of PK2 signals.

Figure 16:
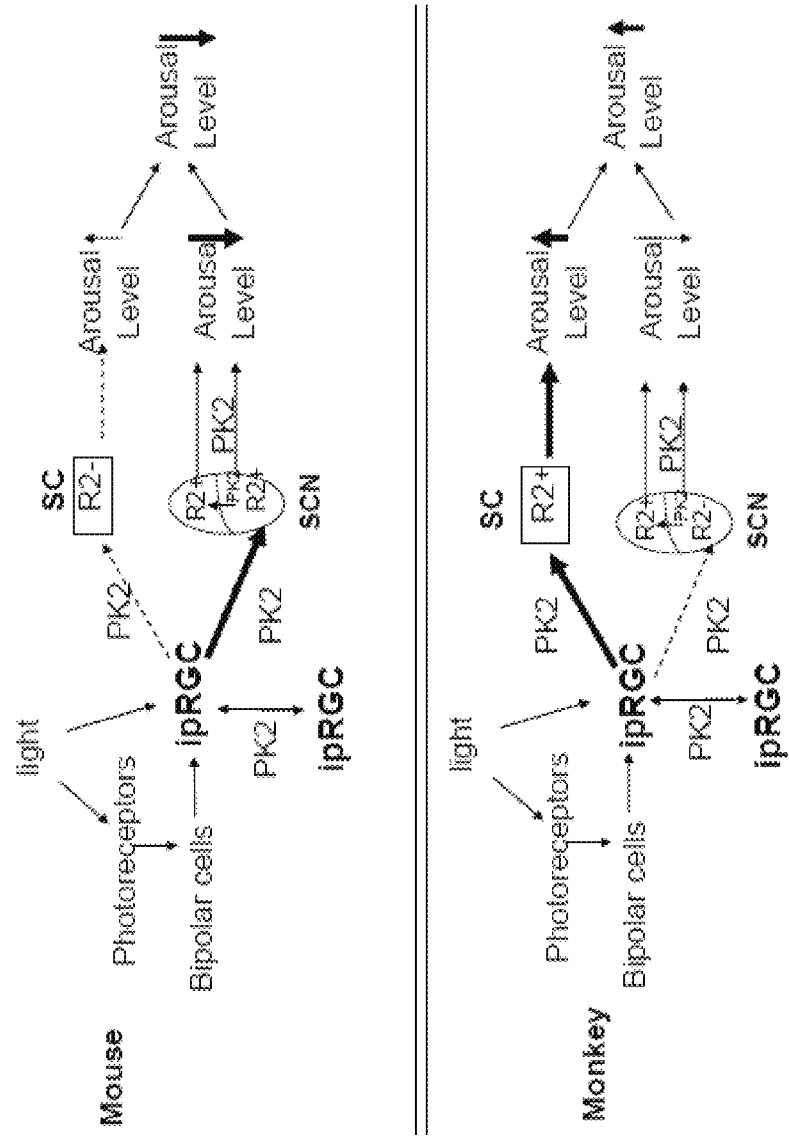
FIG. 16 illustrates a diagram showing the molecular machinery, the coupling and the strategic location of ipRGC and their relationship with critical brain centers for the control of arousal levels in the nocturnal and diurnal mammals, as described in detail in Example 2, below.

Data provided herein for the first time demonstrate that PK2 signaling couples circadian clocks of the ipRGC and then to the brain targets of the ipRGC for the regulation of arousal levels, as schematically illustrated in FIG. 16. FIG. 16 schematically illustrates, as a diagram, the strategic location of ipRGC. ipRGC integrate light/dark and clock information. PK2 signals for the coupling of ipRGC and the neural projection of ipRGC to the critical brain centers for the control of arousal levels in the nocturnal and diurnal mammals.

The molecular machinery and the strategic location of ipRGC enables ipRGC to integrate circadian clock information and environmental light/dark conditions. Further, ipRGC project to brain centers, such as superior colliculus, that are critical for the regulation of the arousal levels and sleep wake cycle. Thus, methods provided herein, which pharmacologically target ipRGC, and in alternative embodiments the receptors expressed in the ipRGC, can be used to treat, ameliorate or prevent ipRGC-regulated and related central nervous disorders, including e.g., photophobia, sleep and mood disorders, seasonal affective disorder, and bipolar disorders.

Photophobia may be caused by overstimulation of the photoreceptors in the retina, or excessive electric impulses to the optic nerve, or excessive response in the brain. As PK2 is involved in communicating the non-visional function of light to the brain, mitigating the PK2 signal via a PK2 antagonist will damp the light signal to the brain. Thus administration of a PK2 antagonist is likely useful for ameliorating, treating, or preventing symptoms of photophobia.

Figure 17:
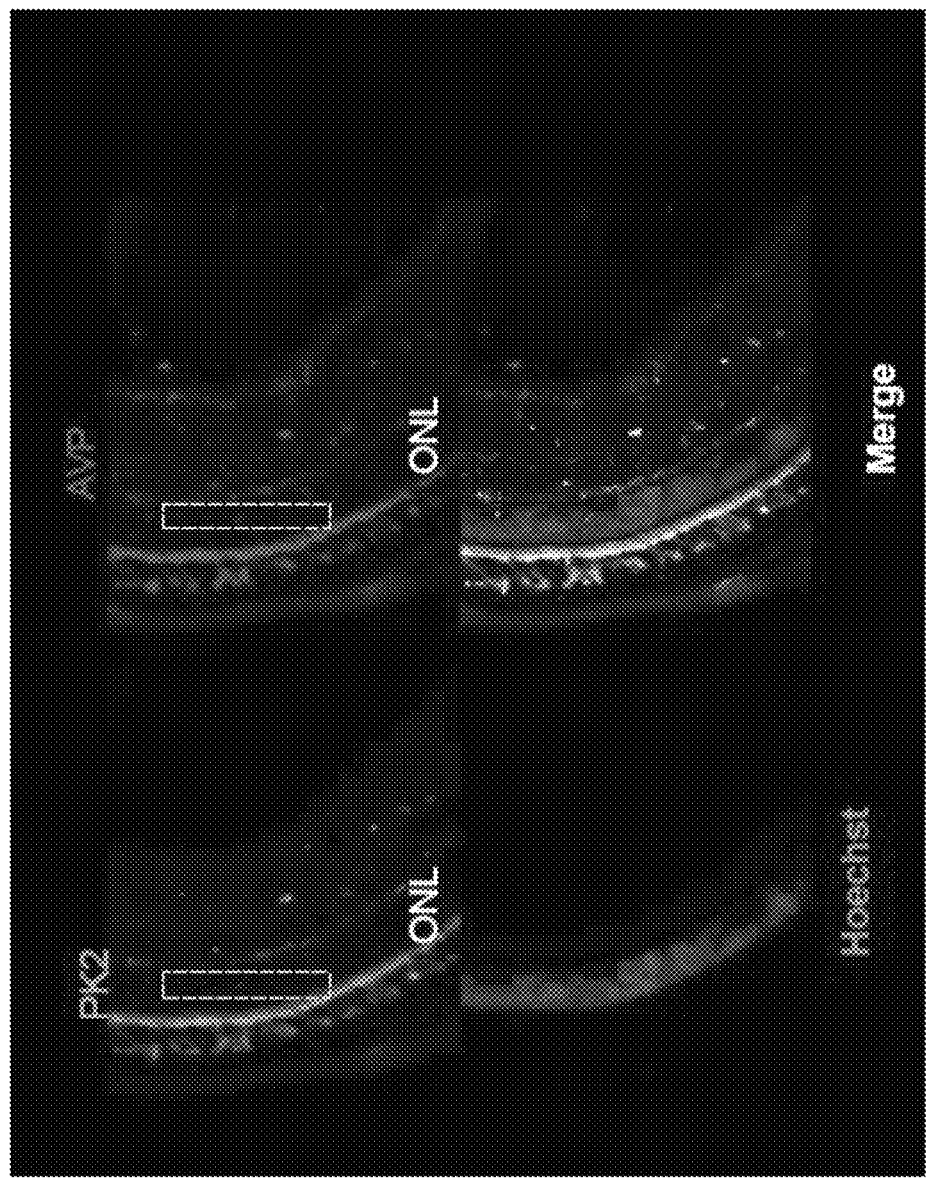
FIG. 17 illustrates images showing the upregulation of vasopressin (AVP) in the outer nuclear layer of retina at CT4, where the upper left panel shows PK2 staining, the upper right panel shows AVP staining, the lower left panel shows Hoeschst staining, and the lower right image is a merge image of the other three panels, as described in detail in Example 2, below.
Figure 18:
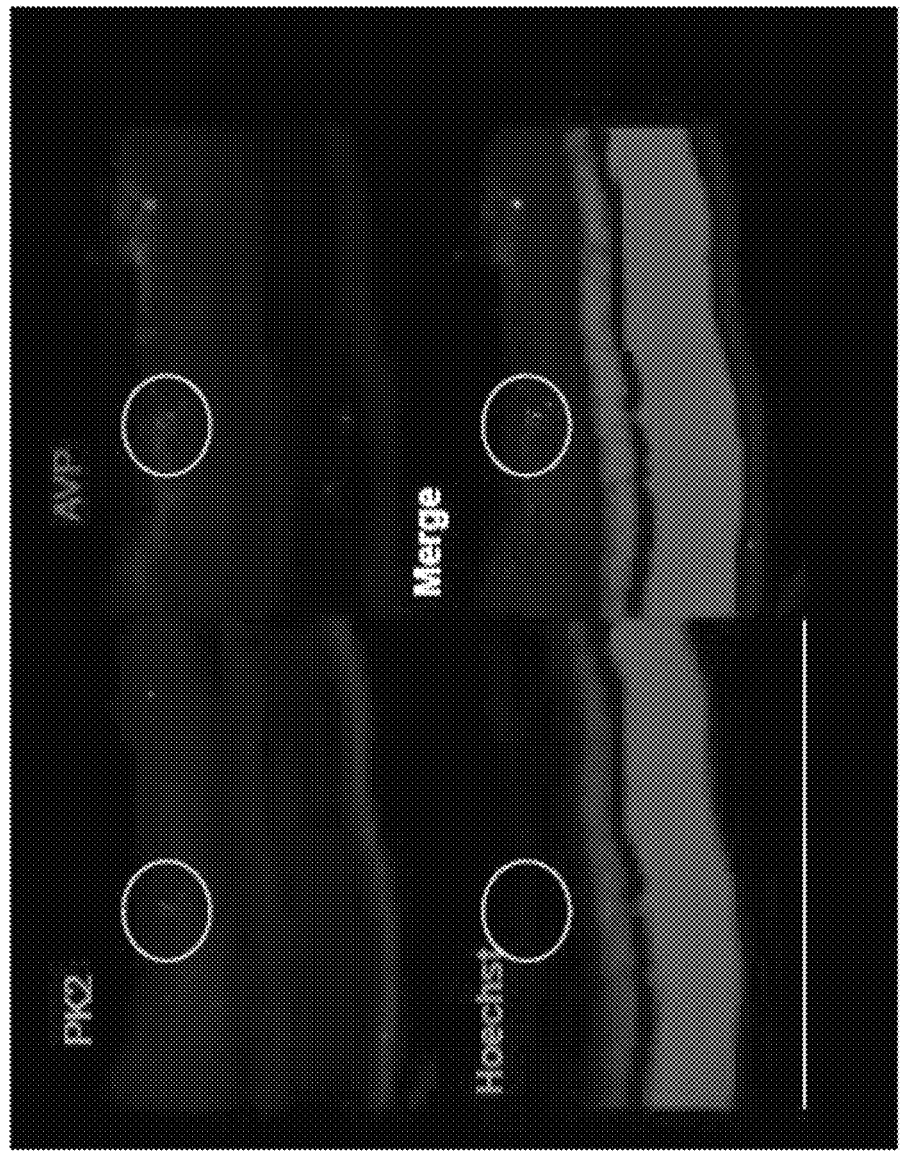
FIG. 18 illustrates that vasopressin (AVP) is also expressed in the ipRGC, where the upper left panel shows PK2 staining, the upper right panel shows AVP staining, the lower left panel shows Hoeschst staining, and the lower right image is a merge image of the other three panels, as described in detail in Example 2, below.

We have shown that vasopressin (AVP) in the outer nuclear layer of retina is also upregulated during continuous darkness, as illustrated in the image of FIG. 17, which illustrates the upregulation of vasopressin (AVP) in the outer nuclear layer of retina at CT4, as with the PK2. Like PK2, vasopressin is also expressed in the ipRGC, as illustrated in the image of FIG. 18, which illustrates colocalization of PK2 with vasopressin (AVP) in the ipRGC. Thus, there appears to have parallel signaling of PK2 and vasopressin for the coupling of the ipRGC, and then from the ipRGC to the critical brain targets. Therefore, the pharmacologic manipulation of vasopressin receptors expressed in the ipRGC will also be useful for treating related central nervous disorders, particularly sleep and mood disorders (seasonal affective disorder, and bipolar disorders).

We have shown that nasal cavity application of PK2 receptor antagonist also promoted sleep in monkeys (FIG. 19). It is likely that PK2 receptor antagonist delivered in this topic route can cross into brain and blocks PK2 receptor in critical nuclei such as the superior colliculi that are innervated by PK2 projections from the ipRGC). FIG. 19 graphically illustrates data showing the effect of a PK2 antagonist (PKRA) on the sleep of monkeys; nasal topic application of PK2 receptor antagonist significantly increased the sleep time of the monkey (*, P<0.05, paired t-test).

Example 3: Compositions for Treating Mammalian Diurnal and Nocturnal Diseases and Related Conditions, and for Treating Other Important Human Disorders Such as Pain, Cancer, Psoriasis and Arthritis This example describes the synthesis and formulation of prokineticin antagonists that can be used to practice the methods and compositions as provided herein.

In alternative embodiments, compounds used to practice methods as provided herein are amide derivatives with interesting solubility and pharmacological profiles. In particular, provided herein are prokineticin antagonists or their prodrugs, including lipid formulations and injectable depot formulation(s) comprising them. These derivatives and their long-acting formulation(s) are suitable for e.g., modifying circadian timing in a mammal, treating psychiatric conditions or symptoms due to alterations in a human circadian regulatory system, treating sleep problems in a mammal, or inducing sleep or activity suppression, or causing an arousal or wakening reaction, and optionally also treating certain human diseases such as cancer, and can be used to practice methods and compositions as provided herein.

In alternative embodiments, compounds used to practice methods as provided herein, in particular, PK2 (prokineticin) receptor antagonists, are amide derivatives and compounds having a structure according to Formula 1 (see, e.g., U.S. Pat. No. 8,722,896):

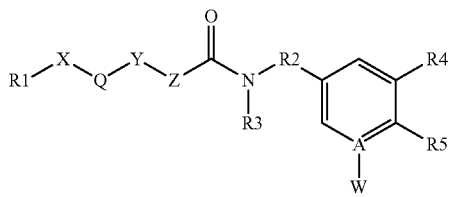

wherein R1 is an optionally substituted aryl, optionally substituted heteroaryl, or an optionally substituted aryl with a fused heterocyclic ring; X and Y are independently lower alkyl; Q is NH or NR6, wherein R6 is lower alkyl; Z is CH2 or CHR7, wherein R7 is lower alkyl; or Q and Z are covalently coupled to each other to form a heterocyclic 4- to 6-membered ring in which Q is N and Z is CH; R2 is lower alkylene; R3 is H, lower alkyl, or alkaryl; A is N or C; W is H, or halogen, or W is null where A is N; and R4 and R5 are independently alkoxy, or are covalently coupled to each other to form an optionally substituted heterocyclic 6- or 7-membered ring with at least one oxygen atom.

In alternative embodiments, R1 is optionally substituted phenyl, optionally substituted indolyl, or optionally substituted indolinyl, and/or X and Y are CH2. Optionally, X and Y are covalently coupled to each other to form a pyrrolidine ring, a piperidine ring, a piperazine ring, a thiomorpholine ring, or a morpholine ring. While not limiting to the inventive subject matter, optionally R3 is an optionally branched lower alky, and/or that R4, R5, W, and the phenyl ring to which R4, R5, and W are covalently coupled form an optionally halogenated benzodioxepin ring. Most typically, R2 is CH2, and/or W is Cl or F.

As many potential clinical indications of prokineticin antagonists are chronic diseases, prolonged inhibition of PK receptors for an extended period are very desirable. Thus, long-acting prokineticin antagonists can be useful for treatment of such human disorders. Long-acting prodrug or long-acting dosage forms of medication can be alternative solutions. Long-acting antagonists, or a sustained release formulation could keep therapeutic levels in patient's systems for days or weeks at a time.

In alternative embodiments, a pharmaceutical composition for modifying circadian timing in a mammal, treating psychiatric conditions or symptoms due to alterations in a human circadian regulatory system, treating sleep problems in a mammal, or inducing sleep or activity suppression, or causing an arousal or wakening reaction, and optionally also treating cancer is provided that comprises a compound according to Formula I or Table 1, below, and a pharmaceutically acceptable carrier. In alternative embodiments, the compound is present in a dosage unit for oral administration in an amount effective to treat or prevent an abnormality associated with cancer, such as a tumor. In alternative embodiments, are uses of a compound according to Formula I in the manufacture of a medicament for modifying circadian timing in a mammal, treating psychiatric conditions or symptoms due to alterations in a human circadian regulatory system, treating sleep problems in a mammal, or inducing sleep or activity suppression, or causing an arousal or wakening reaction, and optionally also treating cancer.

In alternative embodiments, provided are amide derivatives that have a long half-life and/or increased volume of distribution, ideal pharmacokinetics parameters for treating chronic human diseases. In alternative embodiments, provided are amide PK antagonist and formulations that deliver drug over a sustained period of time at concentration efficacious for treatment of human diseases.

In alternative embodiments, provided are compositions and methods for depot delivery of prokineticin antagonists.

In alternative embodiments, provided is: (3R)-1-(benzimidazol-4-ylmethyl)-N-(9-chloro-3,4-dihydro-2H-1,5-benzodioxepin-7-ylmethyl)-N-isobutylpyrrolidine-3-carboxamide.

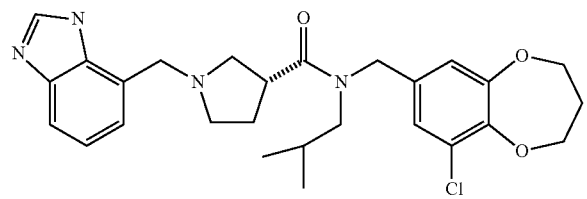 [SMILES: CC(C)CN(Cc1cc(Cl)c2c(c1)OCCCO2)C(=O)[C@@H]1CCN(Cc2cccc3nc[nH]c23)C1]

In alternative embodiments, synthesis comprises:

Step 1. 1H-Benzoimidazole-4-carboxylic acid. 2,3-diaminobenzoic acid (7 g) was suspended in triethyl orthoformate (100 ml) and heated to 130° C. overnight with stirring. After cooling to room temperature, diethyl ether (300 ml) was then added and resulting precipitate filtered. 7.3 g solid powder of 1H-Benzoimidazole-4-carboxylic acid was yielded after drying, M+1=163.1.

Step 2. (1H-Benzoimidazol-4-yl)methanol. 1H-Benzoimidazole-4-carboxylic acid (7.3 g) was suspended in 350 ml of tetrahydrofuran and cooled with dry ice-acetone bath. Lithium aluminium hydride (4M, 21 ml) was slowly added. The reaction was stirred and allowed to warm up to room temperature overnight. The reaction was quenched with 5 ml methanol and extracted with 800 ml of 20% methanol and 80% ethyl acetate. After filtration, solid was discarded. Evaporation of filtrate under reduced pressure resulted in 7 g crude (1H-Benzoimidazol-4-yl)methanol (M+1=149.1) to be used for next step.

Step 3. 1H-Benzoimidazole-4-carbaldehyde. 7 g (1H-Benzoimidazol-4-yl)methanol was dissolved in 350 ml of dimethyl sulfoxide. 36 ml of diisopropylethylamine and 33 g of sulfurtrioxide pyridine complex was added. The reaction was stirred overnight. 800 ml of water was added and the mixture was extracted with 400 ml of ethyl acetate for five times. The organic layers were washed with brine, dried with sodium sulfate and evaporated. Flash chromatography (100% ethyl acetate) yielded yellowish powder of 1H-Benzoimidazole-4-carbaldehyde (M+1=147.1).

Step 4. (3R)-1-(benzimidazol-4-ylmethyl)-N-(9-chloro-3,4-dihydro-2H-1,5-benzodioxepin-7-ylmethyl)-N-isobutylpyrrolidine-3-carboxamide. (3R)-N-(9-chloro-3,4-dihydro-2H-1,5-benzodioxepin-7-ylmethyl)-N-isobutyl pyrrolidine-3-carboxamide was prepared as described. A mixture of (3R)-N-(9-chloro-3,4-dihydro-2H-1,5-benzodioxepin-7-ylmethyl)-N-isobutyl pyrrolidine-3-carboxamide (3800 mg, prepared as described in WO/2010/077976), of 1H-Benzoimidazole-4-carbaldehyde (1550 mg), of glacial acetic acid (4.7 ml), and sodium triacetoxyborohydride (3.0 g) in dichloromethane (150 ml) was stirred overnight. After the addition of aq. K2CO3 (2N, 1200 mL), the mixture was extracted with 100 ml of ethyl acetate three times. Organic layers were combined, washed with brine (500 ml), dried over anhydrous sodium sulfate, and concentrated. The residue was purified via flash chromatography on silica (100% ethyl acetate in hexane) and yielded (3R)-1-(benzimidazol-4-ylmethyl)-N-(9-chloro-3,4-dihydro-2H-1,5-benzodioxepin-7-ylmethyl)-N-isobutylpyrrolidine-3-carboxamide as a resin: MS (m+1)=497.2; H NMR (500 MHz, CDCl3) 0.95 (m, 6H), 2.00 (m, 1H), 2.09 (s, 1H), 2.12 (m, 1H), 2.25 (m, 2H), 2.39 (m, 1H), 2.45 (m, 1H), 2.53 (m, 1H), 2.60 (m, 1H), 2.70 (m, 1H), 3.14 (m, 1H), 3.23 (m, 1H), 3.30 (m, 1H), 3.38 (q, 1H), 4.20 (m, 2H), 4.30 (m, 2H), 4.45 (m, 2H), 4.66 (d, 1H), 6.6-8.0 (m, 6H).

In alternative embodiments, provided is: (3R)-1-(benzimidazol-4-ylmethyl)-N-(9-chloro-3,4-dihydro-2H-1,5-benzodioxepin-7-ylmethyl)-N-isobutylpyrrolidine-3-carboxamide hydrochloride salt.

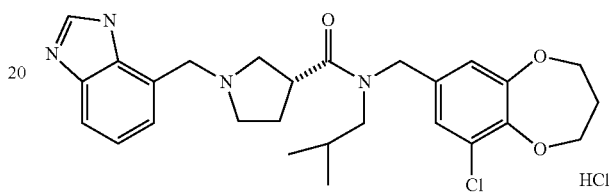

In alternative embodiments, synthesis comprises:

Step 1. 1,77 g of (3R)-1-(benzimidazol-4-ylmethyl)-N-(9-chloro-3,4-dihydro-2H-1,5-benzodioxepin-7-ylmethyl)-N-isobutylpyrrolidine-3-carboxamide was dissolved in 20 ml dichloromethane. 4M hydrochloride in 1, 4-dioxane was added, and stirred for 4 hr at room temperature. The mixture was evaporated under reduce pressure to yield (3R)-1-(benzimidazol-4-ylmethyl)-N-(9-chloro-3,4-dihydro-2H-1, 5-benzodioxepin-7-ylmethyl)-N-isobutylpyrrolidine-3-carboxamide hydrochloride salt. Melting point, 120-122° C.

In alternative embodiments, provided is: (–)-(2R)-2-Methyl-3-(benzimidazol-4-ylmethylamino)-N-(9-chloro-3,4-dihydro-2H-1,5-benzodioxepin-7-ylmethyl)-N-isobutylpropanamide.

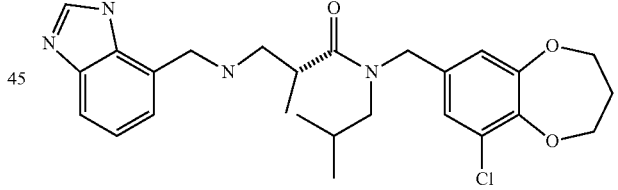

Utilizing (–)-(2R)-2-Methyl-3-amino-N-(9-chloro-3,4-dihydro-2H-1,5-benzodioxepin-7-ylmethyl)-N-isobutylpropanamide, which was prepared as described (WO/2010/077976), (–)-(2R)-2-Methyl-3-(benzimidazol-4-ylmethylamino)-N-(9-chloro-3,4-dihydro-2H-1,5-benzodioxepin-7-ylmethyl)-N-isobutylpropanamide was prepared described above.

Selected Biological Experimental Examples

In Vitro $Ca^{2+}$ Mobilization Assay

An aequorin-based luminescent assay for calcium mobilization was used to measure mobilization of intracellular $Ca^{2+}$ (Bullock et al., Mol Pharmacol 65, 582-588, 2004). Chinese hamster ovary (CHO) cells stably expressing photoprotein aequorin and recombinant PKR1 or PKR2 were tested by this method. Briefly, the cells were charged in Opti-MEM™ (Invitrogen) containing 8 μM of coelenterazine cp at 37° C. for 2 hours. Cells were detached by brief trypsinization and maintained in Hank's Balanced Salt Solution (HBSS) plus 10 mM HEPES (pH7.5) and 0.1% BSA at about $5 \times 10^5$ cells/ml. Luminescence measurements were made using a Berthold luminometer.

All compounds were diluted in HBSS plus 10 mM HEPES (pH7.5) and 0.1% BSA. To test the agonist activity, 100 μl of cells were injected into the tubes with 20 μl of compounds. For antagonist assays, 80 μl cells were incubated in the tubes with 20 μl different concentrations of antagonists at room temperature for 20 minutes, and then 100 μl of recombinant PK2 were injected. The IC50 obtained from the assays were then converted to Ki values using the formula: $IC50/(1+[PK2]/EC50_{PK2})$.

In some embodiments, the numbers expressing quantities of ingredients, properties such as concentration, reaction conditions, and so forth, used to describe and claim certain embodiments provided herein are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments provided herein are approximations, the numerical values set forth in the specific examples are reported as precisely as practicable. The numerical values presented in some embodiments provided herein may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate embodiments provided herein and does not pose a limitation on the scope of the invention otherwise claimed. No language in the specification should be construed as indicating any non-claimed element essential to the practice of the invention.

Groupings of alternative elements or embodiments disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

TABLE 1

| Structure | Compound Name | Mass Ion (M + 1) | Ki for PKR2 (nM) | Ki for PKR1 (nM) |
|---|---|---|---|---|
| 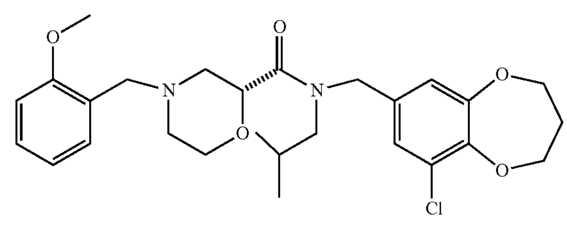 | (−)-(2R)-1-(2-Methoxybenzyl)-N-(9-chloro-3,4-dihydro-2H-1,5-benzodioxepin-7-ylmethyl)-N-isobutylmorpholine-2-carboxamide | 503.1 | | 1.49 |
| 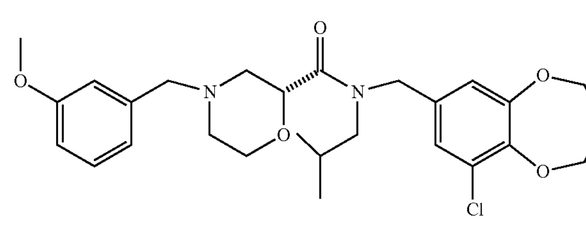 | (−)-(2R)-1-(3-Methoxybenzyl)-N-(9-chloro-3,4-dihydro-2H-1,5-benzodioxepin-7-ylmethyl)-N-isobutylmorpholine-2-carboxamide | 503.1 | | 2.50 |

TABLE 1-continued

| Structure | Compound Name | Mass Ion (M + 1) | Ki for PKR2 (nM) | Ki for PKR1 (nM) |
|---|---|---|---|---|
| 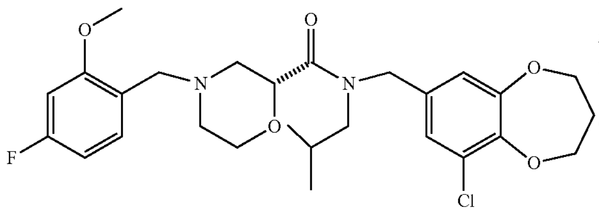 | (−)-(2R)-1-(4-Fluoro-2-methoxybenzyl)-N-(9-chloro-3,4-dihydro-2H-1,5-benzodioxepin-7-ylmethyl)-N-isobutylmorpholine-2-carboxamide | 521.2 | | 7.3 |
| 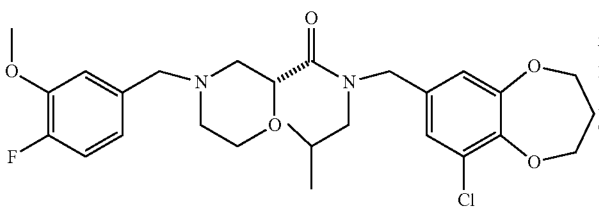 | (−)-(2R)-1-(4-Fluoro-3-methoxybenzyl)-N-(9-chloro-3,4-dihydro-2H-1,5-benzodioxepin-7-ylmethyl)-N-isobutylmorpholine-2-carboxamide | 521.2 | 1.9 2.6 | 5.4 |
| 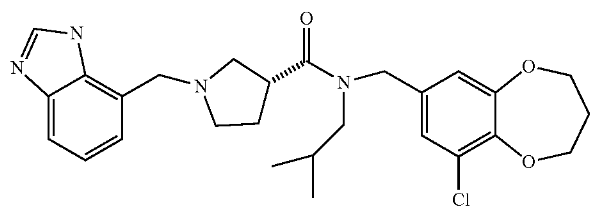 | (−)-(3R)-1-(benzimidazol-4-ylmethyl)-N-(9-chloro-3,4-dihydro-2H-1,5-benzodioxepin-7-ylmethyl)-N-isobutylpyrrolidine-3-carboxamide | 497.3 | 1.7 | 2.6 |
| 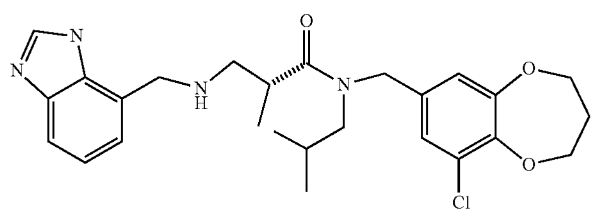 | (−)-(2R)-2-Methyl-3-(benzimidazol-4-ylmethylamino)-N-(9-chloro-3,4-dihydro-2H-1,5-benzodioxepin-7-ylmethyl)-N-isobutylpropanamide | 485.3 | 3.5 | 4.2 |
| 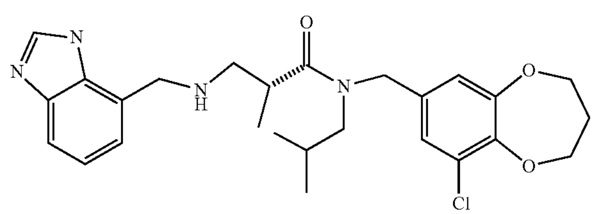 | (±)-2-Methyl-3-(benzimidazol-4-ylmethylamino)-N-(9-chloro-3,4-dihydro-2H-1,5-benzodioxepin-7-ylmethyl)-N-isobutylpropanamide | 485.3 | 2.1 | 5.6 |
| | (−)-(3R)-1-(5-fluoro-benzimidazol-4-ylmethyl)-N-(9-chloro-3,4-dihydro-2H-1,5-benzodioxepin-7-ylmethyl)-N-isobutylpyrrolidine-3-carboxamide | 515.3 | | 71.3 |
| 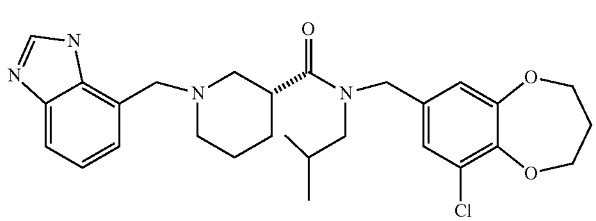 | (−)-(3R)-1-(benzimidazol-4-ylmethyl)-N-(9-chloro-3,4-dihydro-2H-1,5-benzodioxepin-7-ylmethyl)-N-isobutylpiperidine-3-carboxamide | 511.3 | 3.0 | 97 |

TABLE 1-continued

| Structure | Compound Name | Mass Ion (M + 1) | Ki for PKR2 (nM) | Ki for PKR1 (nM) |
|---|---|---|---|---|
| 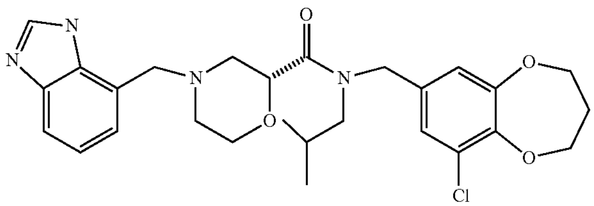 | (−)-(2R)-1-(benzimidazol-4-ylmethyl)-N-(9-chloro-3,4-dihydro-2H-1,5-benzodioxepin-7-ylmethyl)-N-isobutylpiperidine-2-carboxamide | 513.3 | 1.3 | 8.4 |
| 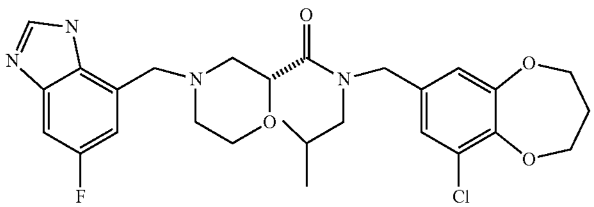 | (−)-(2R)-1-(5-fluro-benzimidazol-4-ylmethyl)-N-(9-chloro-3,4-dihydro-2H-1,5-benzodioxepin-7-ylmethyl)-N-isobutylmorpholine-2-carboxamide | 531.3 | | 6.14 |
| 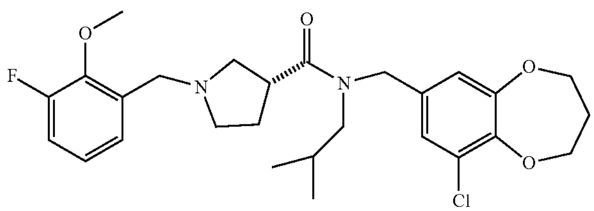 | (−)-(3R)-1-(3-Fluoro-2-methoxybenzyl)-N-(9-chloro-3,4-dihydro-2H-1,5-benzodioxepin-7-ylmethyl)-N-isobutylpyrrolidine-3-carboxamide | 505.3 | | 170 |
| 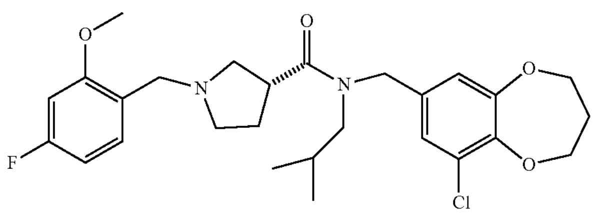 | (−)-(3R)-1-(4-Fluoro-2-methoxybenzyl)-N-(9-chloro-3,4-dihydro-2H-1,5-benzodioxepin-7-ylmethyl)-N-isobutylpyrrolidine-3-carboxamide | 505.3 | | 9.32 |
| 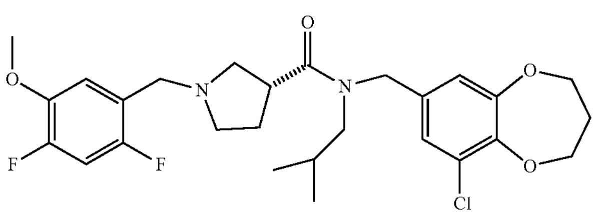 | (−)-(3R)-1-(4,6-Difluoro-3-methoxybenzyl)-N-(9-chloro-3,4-dihydro-2H-1,5-benzodioxepin-7-ylmethyl)-N-isobutylpyrrolidine-3-carboxamide | 523.3 | | 6.14 |
| 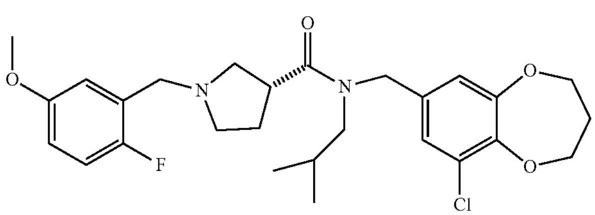 | (−)-(3R)-1-(6-Fluoro-3-methoxybenzyl)-N-(9-chloro-3,4-dihydro-2H-1,5-benzodioxepin-7-ylmethyl)-N-isobutylpyrrolidine-3-carboxamide | 505.4 | | 301 |
| 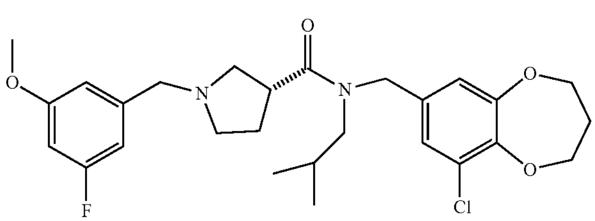 | (−)-(3R)-1-(5-Fluoro-3-methoxybenzyl)-N-(9-chloro-3,4-dihydro-2H-1,5-benzodioxepin-7-ylmethyl)-N-isobutylpyrrolidine-3-carboxamide | 505.4 | | 373 |

TABLE 1-continued

| Structure | Compound Name | Mass Ion (M + 1) | Ki for PKR2 (nM) | Ki for PKR1 (nM) |
|---|---|---|---|---|
| 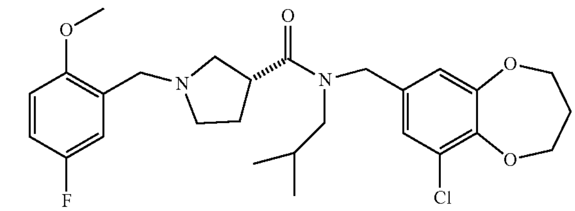 | (−)-(3R)-1-(5-Fluoro-2-methoxybenzyl)-N-(9-chloro-3,4-dihydro-2H-1,5-benzodioxepin-7-ylmethyl)-N-isobutylpyrrolidine-3-carboxamide | 505.4 | 9.3 | 6.9 |
| 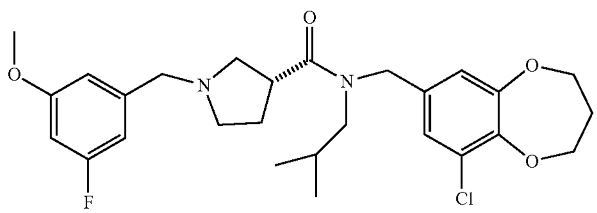 | (−)-(3R)-1-(5-Fluoro-3-methoxybenzyl)-N-(9-chloro-3,4-dihydro-2H-1,5-benzodioxepin-7-ylmethyl)-N-isobutylpyrrolidine-3-carboxamide | 505.4 | 41.5 | |
| 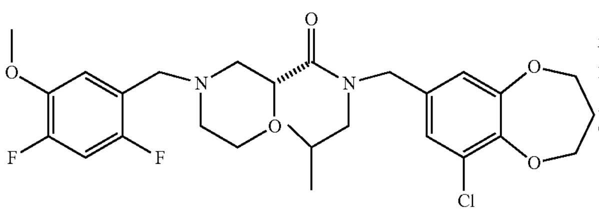 | (−)-(2R)-1-(4,6-Difluoro-3-methoxybenzyl)-N-(9-chloro-3,4-dihydro-2H-1,5-benzodioxepin-7-ylmethyl)-N-isobutylmorpholine-2-carboxamide | 539.2 | 4.09 | |
| 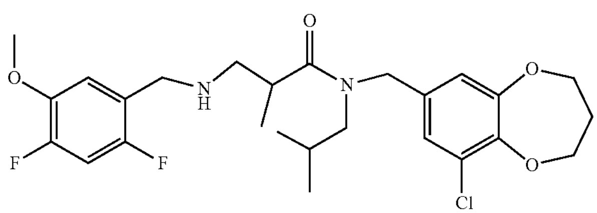 [SMILES: COc1cc(CNCC(C)C(=O)N(Cc2cc(Cl)c3c(c2)OCCCO3)CC(C)C)c(F)cc1F] | (±)-2-Methyl-3-((3-methoxy-4,6-difluoro)benzylamino)-N-(9-chloro-3,4-dihydro-2H-1,5-benzodioxepin-7-ylmethyl)-N-isobutylpropanamide | 511.1 | 43.5 | |
| 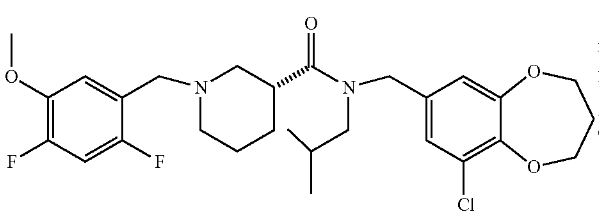 | (−)-(3R)-1-(4,6-Difluoro-3-methoxybenzyl)-N-(9-chloro-3,4-dihydro-2H-1,5-benzodioxepin-7-ylmethyl)-N-isobutylpiperidine-3-carboxamide | 536.9 | 13.8 | |
| 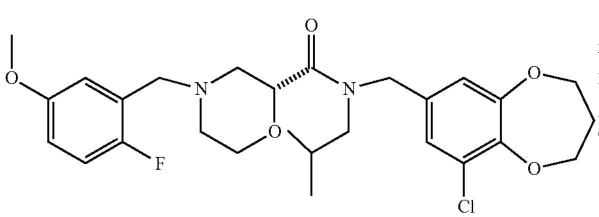 | (−)-(2R)-1-(6-Fluoro-3-methoxybenzyl)-N-(9-chloro-3,4-dihydro-2H-1,5-benzodioxepin-7-ylmethyl)-N-isobutylmorpholine-2-carboxamide | 520.9 | 10.0 | |
| 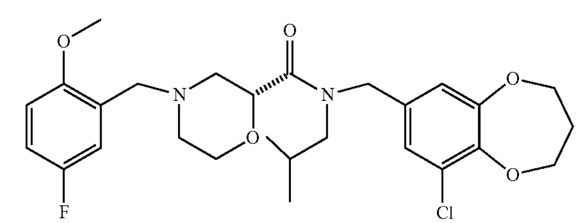 | (−)-(2R)-1-(5-Fluoro-2-methoxybenzyl)-N-(9-chloro-3,4-dihydro-2H-1,5-benzodioxepin-7-ylmethyl)-N-isobutylmorpholine-2-carboxamide | 521.0 | 7.3 | |

TABLE 1-continued

| Structure | Compound Name | Mass Ion (M + 1) | Ki for PKR2 (nM) | Ki for PKR1 (nM) |
|---|---|---|---|---|
| 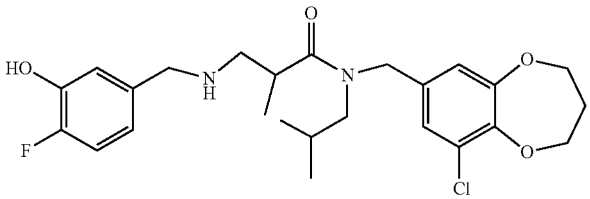 [SMILES: CC(C)CN(Cc1cc(Cl)c2c(c1)OCCCO2)C(=O)C(C)CNCc1ccc(F)c(O)c1] | (±)-2-Methyl-3-((3-hydroxy-4-fluoro)benzylamino)-N-(9-chloro-3,4-dihydro-2H-1,5-benzodioxepin-7-ylmethyl)-N-isobutylpropanamide | 479.4 | | 4.4 |
| 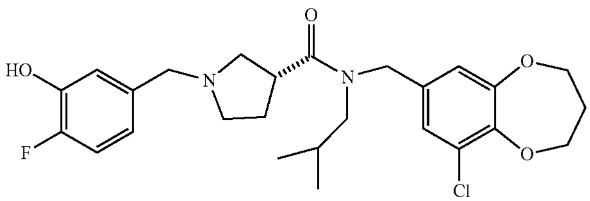 | (−)-(3R)-1-(4-Fluoro-3-hydroxybenzyl)-N-(9-chloro-3,4-dihydro-2H-1,5-benzodioxepin-7-ylmethyl)-N-isobutylpyrrolidine-3-carboxamide | 491.4 | | 107 |

In alternative embodiments, listed in Table 1 are novel compounds provided herein, each of which can be used to practice methods as provided herein. These compounds were prepared using the foregoing methodology by varying the starting materials, reagents or conditions used. The requisite reagents were either commercially available or described in the literature or readily synthesized by one skilled in the art.

Based on the inventors' discovery of biological activity of contemplated compounds, it is generally contemplated that the compounds provided herein can be formulated for modifying circadian rhythmicity or timing in a mammal, treating psychiatric conditions or symptoms due to alterations in a human circadian regulatory system, treating sleep problems in a mammal, or inducing sleep or activity suppression, or causing an arousal or wakening reaction, and optionally also treating various cancers. In alternative embodiments, provided are pharmaceutical compositions comprising compounds described herein, wherein these compounds are effective for modifying circadian rhythmicity or timing in a mammal, treating psychiatric conditions or symptoms due to alterations in a human circadian regulatory system, treating sleep problems in a mammal, or inducing sleep or activity suppression, or causing an arousal or wakening reaction, and optionally also treating or preventing various types of cancers, wherein contemplated pharmaceutical compositions comprise a therapeutically effective amount of contemplated compounds (or pharmaceutically acceptable salt, hydrate, or prodrug thereof), and a pharmaceutically acceptable carrier. For example, in one aspect, compositions are formulated for treatment of glioma, pancreatic cancers or other tumors.

In alternative embodiments, provided are compositions formulated with one or more non-toxic pharmaceutically acceptable carriers. In alternative embodiments, provided are pharmaceutical compositions formulated for oral administration in solid, semi-solid, or liquid form, or for parenteral injection. In alternative embodiments, these pharmaceutical compositions can be administered to humans and other animals using various routes, including orally, rectally, parenterally, intraperitoneally, vaginally, or topically.

In alternative embodiments, provided are pharmaceutical compositions for injection, e.g., that comprise pharmaceutically acceptable sterile aqueous or nonaqueous solutions, dispersions, emulsions, or suspensions, as well as sterile powders for reconstitution into sterile injectable solutions or dispersions prior to use. Examples of suitable aqueous and nonaqueous carriers, diluents, solvents, or vehicles include water, ethanol, polyols (e.g., glycerol, propylene glycol, polyethylene glycol, etc.), and suitable mixtures thereof, oils, and injectable organic esters (e.g., ethyl oleate). In alternative embodiments, provided are compositions that comprise or contain various inactive ingredients, including preservatives, wetting agents, emulsifying agents, and/or dispersing agents. Sterility may be ensured by inclusion of antibacterial and/or antifungal agents (e.g., paraben, phenol sorbic acid, chlorobutanol, etc.). Where appropriate, osmotically active agents may be included (e.g., sugars, sodium chloride, etc.).

In alternative embodiments, provided are compositions formulated into solid or semi-solid dosage forms for oral administration, and may therefore be ointments, capsules, tablets, pills, powders, and granules. In alternative embodiments, solid or semi-solid dosage forms, contemplated compound are mixed with at least one of a pharmaceutically acceptable excipient or carrier (e.g., sodium citrate or dicalcium phosphate), a filler or extender (e.g., starch, lactose, sucrose, glucose, mannitol, or silicic acid), a binder (e.g., carboxymethylcellulose, alginates, gelatin, polyvinylpyrrolidone, sucrose, etc.), a humectant (e.g., glycerol), a disintegrating agent (e.g., agar-agar, calcium carbonate, potato or tapioca starch, alginic acid, certain silicates, or sodium carbonate), a solution retarding agent (e.g., paraffin), an absorption accelerator (e.g., quaternary ammonium compound), a wetting agents (e.g., cetyl alcohol and glycerol monostearate), and absorbents (e.g., kaolin, or bentonite clay), and a lubricant (e.g., talc, calcium stearate, magnesium stearate, solid polyethylene glycols, sodium lauryl sulfate).

In alternative embodiments, solid or semi-solid compositions of a similar type may also be employed as fillers in soft and hard-filled gelatin capsules using such excipients as lactose or milk sugar as well as high molecular weight polyethylene glycols and the like. The solid or semi-solid dosage forms of tablets, dragees, capsules, pills, and granules can be prepared with coatings and shells such as enteric coatings and other coatings well known in the pharmaceutical formulating art. In alternative embodiments, provided are compositions formulated to release the active ingredient (s) only, or alternatively, in a certain part of the intestinal tract, optionally, in a delayed manner. Examples of embedding compositions which can be used include polymeric substances and waxes. In alternative embodiments, provided are compounds in micro-encapsulated form, if appropriate, with one or more of the above-mentioned excipients.

In alternative embodiments, provided are liquid dosage forms for oral administration including pharmaceutically acceptable emulsions, solutions, suspensions, syrups and elixirs. In addition to the active compounds, liquid dosage forms may contain inert diluents commonly used in the art (e.g., water, or other solvent, solubilizing agents), emulsifiers (e.g., ethyl alcohol, isopropyl alcohol, ethyl carbonate, ethyl acetate, benzyl alcohol, benzyl benzoate, propylene glycol, 1,3-butylene glycol, dimethyl formamide), oils (and in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, and perfuming agents.

In alternative embodiments, provided are compositions for rectal or vaginal administration, e.g., suppositories which can be prepared by mixing the compounds provided herein with suitable non-irritating excipients or carriers such as cocoa butter, polyethylene glycol or a suppository wax which are solid or semi-solid at room temperature but liquid at body temperature and therefore melt in the rectum or vaginal cavity and release the active compound.

In alternative embodiments, provided are compounds to be administered in form of liposomes, which may be unilamellar, oligolamellar, or polylamellar. Contemplated compositions in liposome form may further contain stabilizers, preservatives, excipients, etc. In alternative embodiments, provided are lipids for liposome formation including phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Actual dosage levels of compounds in pharmaceutical compositions provided herein may be varied so as to obtain an amount of contemplated compound(s) that is effective to achieve the desired therapeutic response for a particular patient, composition, and mode of administration. Thus, the selected dosage level will depend upon various factors, including the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In alternative embodiments, provided are dosage levels of about 0.01 mg to about 500 mg, or about 0.5 mg to about 50 mg of contemplated compound per kilogram of body weight per day are administered orally to a mammalian patient. If desired, the effective daily dose may be divided into multiple doses for purposes of administration, e.g., two to four separate doses per day.

In alternative embodiments, provided are pharmaceutical compositions comprising additional pharmaceutically active compounds. In alternative embodiments, additional pharmaceutically active compounds may be included in the same pharmaceutical composition, or may be administered separately, and a person of ordinary skill in the art will readily determine schedule and route of suitable co-administration of the additional pharmaceutically active compounds. In alternative embodiments, provided are compositions may also include metabolites and/or prodrug forms of contemplated compounds, and that all compounds may be present in racemic mixture or stereochemically pure (or partially purified) form.

REFERENCES—EXAMPLE 1

1. Lincoln, et al., Temporal expression of seven clock genes in the suprachiasmatic nucleus and the pars tuberalis of the sheep: evidence for an internal coincidence timer. *Proc Natl Acad Sci USA* 99, 13890-13895 (2002)
2. Valenzuela, F. J. et al. Clock gene expression in adult primate suprachiasmatic nuclei and adrenal: is the adrenal a peripheral clock responsive to melatonin? *Endocrinology* 149, 1454-1461 (2008)
3. Schwartz et al., In vivo metabolic activity of the suprachiasmatic nuclei: a comparative study. *Brain Res.* 1983 274, 184-7 (1983)
4. Smale, et al., Mammalian diurnality: some facts and gaps. *J Biol Rhythms* 18, 356-366 (2003)
5. Jin, X. et al. A molecular mechanism regulating rhythmic output from the suprachiasmatic circadian clock. *Cell* 96, 57-68 (1999)
6. Cheng, M. Y. et al. Prokineticin 2 transmits the behavioural circadian rhythm of the suprachiasmatic nucleus. *Nature* 417, 405-410 (2002)
7. Burton, K. J., et al. Expression of prokineticin 2 and its receptor in the Macaque monkey brain. *Chronobiology International* In Press DOI:10.3109/07420528.2015.1125361
8. Mistlberger, R. E. Circadian regulation of sleep in mammals: role of the suprachiasmatic nucleus. *Brain Res Brain Res Rev.* 49, 429-454 (2005)
9. Moore, R. Y. The suprachiasmatic nucleus and the circadian timing system. *Prog Mol Biol Transl Sci.* 119, 1-28 (2013)
10. Mrosovsky, N. Masking: history, definitions, and measurement. *Chronobiol Int.* 16, 415-429 (1999)
11. Morin, L. P. Neuroanatomy of the extended circadian rhythm system. *Exp Neurol.* 243, 4-20 (2013)
12. Borbély, A. A. Effects of light on sleep and activity rhythms. *Prog Neurobiol.* 10, 1-31 (1978)
13. Gander, P. H. & Moore-Ede, M. C. Light-dark masking of circadian temperature and activity rhythms in squirrel monkeys. *Am J Physiol.* 245, R927-934 (1983)
14. Campbell, S. S. & Dawson, D. Enhancement of nighttime alertness and performance with bright ambient light. *Physiol Behav.* 48, 317-320 (1990)
15. Rietveld, W. J., Minors, D. S. & Waterhouse, J. M. Circadian rhythms and masking: an overview. *Chronobiol Int.* 10, 306-312 (1993)
16. Provencio, I. et al. A novel human opsin in the inner retina. *J Neurosci.* 20, 600-605 (2000)
17. Berson, D. M., Dunn, F. A. & Takao, M. Phototransduction by retinal ganglion cells that set the circadian clock. *Science* 295, 1070-1073 (2002)
18. Mrosovsky, N. & Hattar, S. Impaired masking responses to light in melanopsin-knockout mice. *Chronobiol Int.* 20, 989-999 (2003)
19. Dacey, D. M. et al. Melanopsin-expressing ganglion cells in primate retina signal colour and irradiance and project to the LGN. *Nature* 433, 749-754 (2005)

20. Panda, S. et al. Melanopsin is required for non-image-forming photic responses in blind mice. *Science* 301, 525-527 (2003)
21. Wee, et al., Loss of photic entrainment and altered free-running circadian rhythms in math5−/− mice. *J Neurosci.* 22, 10427-10433 (2002)
22. Altimus, C. M. et al. Rods-cones and melanopsin detect light and dark to modulate sleep independent of image formation. *Proc Natl Acad Sci USA* 105, 19998-20003 (2008)
23. Goz, D. et al. Targeted destruction of photosensitive retinal ganglion cells with a saporin conjugate alters the effects of light on mouse circadian rhythms. *PLoS One* 3, e3153 (2008)
24. Güler, A. D. et al. Melanopsin cells are the principal conduits for rod-cone input to non-image-forming vision. *Nature* 453, 102-105 (2008)
25. Hatori, M. et al. Inducible ablation of melanopsin-expressing retinal ganglion cells reveals their central role in non-image forming visual responses. *PLoS One* 3, e2451 (2008)
26. Johnson, et al., Loss of entrainment and anatomical plasticity after lesions of the hamster retinohypothalamic tract. *Brain Res.* 460, 297-313 (1988)
27. Li, et al., Disruption of masking by hypothalamic lesions in Syrian hamsters. *J Comp Physiol A Neuroethol Sens Neural Behav Physiol.* 191, 23-30 (2005)
28. Lehman, M. N. et al. Circadian rhythmicity restored by neural transplant. Immunocytochemical characterization of the graft and its integration with the host brain. *J Neurosci.* 7, 1626-1638 (1987)
29. Li, J. D. et al. Attenuated circadian rhythms in mice lacking the prokineticin 2 gene. *J Neurosci.* 26, 11615-11623 (2006)
30. Prosser, H. M. et al. Prokineticin receptor 2 (Prokr2) is essential for the regulation of circadian behavior by the suprachiasmatic nuclei. *Proc Natl Acad Sci USA* 104, 648-653 (2007)
31. Hu, W. P. et al. Altered circadian and homeostatic sleep regulation in prokineticin 2-deficient mice. *Sleep* 30, 247-256 (2007)
32. Lupi, D., Oster, H., Thompson, S. & Foster, R. G. The acute light-induction of sleep is mediated by OPN4-based photoreception. *Nat Neurosci.* 11, 1068-1073 (2008).
33. Tsai, J. W. et al. Melanopsin as a sleep modulator: circadian gating of the direct effects of light on sleep and altered sleep homeostasis in Opn4 (−/−) mice. *PLoS Biol.* 7, e1000125 (2009)
34. Morin, et al., Retinal ganglion cell projections to the hamster suprachiasmatic nucleus, intergeniculate leaflet, and visual midbrain: bifurcation and melanopsin immunoreactivity. *J Comp Neurol.* 465, 401-416 (2003)
35. Hattar, S. et al. Central projections of melanopsin-expressing retinal ganglion cells in the mouse. *J. Comp. Neurol.* 497, 326-349 (2006)
36. Hannibal, J. et al. Central projections of intrinsically photosensitive retinal ganglion cells in the macaque monkey. *J Comp Neurol.* 522, 2231-2248 (2014)
37. Cheng, M. Y., Leslie, F. M. & Zhou, Q. Y. Expression of prokineticins and their receptors in the adult mouse brain. *J Comp Neurol.* 498, 796-809 (2006)
38. Moore, R. Y. & Silver, R. Suprachiasmatic nucleus organization. *Chronobiol Int.* 15, 475-487 (1998)
39. Yuill, et al., Prokineticin 2 depolarizes paraventricular nucleus magnocellular and parvocellular neurons. *Eur J Neurosci.* 25, 425-434 (2007)
40. Ren, P. et al. Prokineticin 2 regulates the electrical activity of rat suprachiasmatic nuclei neurons. *PLoS One* 6, e20263 (2011)
41. Costa, M. S. et al. Retinohypothalamic projections in the common marmoset (Callithrix jacchus): A study using cholera toxin subunit B. *J Comp Neurol.* 415, 393-403 (1999)
42. Denny-Brown, D. The midbrain and motor integration. *Proc. R. Sot. Med.* 55, 527-538 (1962)
43. Dean, et al., Visual desynchronization of cortical EEG impaired by lesions of superior colliculus in rats. *J Neurophysiol.* 52, 625-637 (1984)
44. Dean, P., Redgrave, P. & Westby, G. W. Event or emergency? Two response systems in the mammalian superior colliculus. *Trends Neurosci.* 12, 137-147 (1989)
45. May, P. J. The mammalian superior colliculus: laminar structure and connections. *Prog Brain Res.* 151, 321-378 (2006)
46. Berman, et al., Functional identification of a pulvinar path from superior colliculus to cortical area MT. *J Neurosci.* 30, 6342-6354 (2010)
47. Lyon, et al., A disynaptic relay from superior colliculus to dorsal stream visual cortex in macaque monkey. *Neuron.* 65, 270-279 (2010)
48. Hilbig, et al., Dendritic organization of neurons of the superior colliculus in animals with different visual capability. *Brain Res Bull.* 51, 255-265 (2000)
49. Chalfin, et al., Scaling of neuron number and volume of the pulvinar complex in New World primates: comparisons with humans, other primates, and mammals. *J Comp Neurol.* 504, 265-274 (2007)
50. Crompton, et al., Evolution of homeothermy in mammals. *Nature* 272, 333-336 (1978)
51. Zhang, et al., Efferent projections of prokineticin 2 expressing neurons in the mouse suprachiasmatic nucleus. *PLoS One* 4, e7151 (2009)
52. Ghosh, A. et al. Anti-inflammatory and neuroprotective effects of an orally active apocynin derivative in pre-clinical models of Parkinson's disease. *J Neuroinflammation* 9, 241 (2012).
53. Qiu C. Y. et al. Prokineticin 2 potentiates acid-sensing ion channel activity in rat dorsal root ganglion neurons. *J Neuroinflammation.* 9, 108 (2012).
54. Jones, C. R. et al. Familial advanced sleep-phase syndrome: A short-period circadian rhythm variant in humans. *Nat Med.* 5, 1062-1065 (1999).
55. Evans D. S. et al. Common genetic variants in ARNTL and NPAS2 and at chromosome 12p13 are associated with objectively measured sleep traits in the elderly. *Sleep* 36, 431-46 (2013).
56. Rahman K, Burton A, Galbraith S, Lloyd A, Vollmer-Conna U. Sleep-wake behavior in chronic fatigue syndrome. *Sleep* 34, 671-8 (2011).
57. Mehra R. et al. Interpreting wrist actigraphic indices of sleep in epidemiologic studies of the elderly: the Study of Osteoporotic Fractures. *Sleep* 31, 1569-76 (2008).
58. Fletcher, R. B., Amemori, K. I., Goodwin, M. & Graybiel, A. M. 34th Annual International Conference of the IEEE EMBS. 4046-4049 (2012).
59. Balzamo, et al., Scoring of sleep and wakefulness by behavioral analysis from video recordings in rhesus monkeys: comparison with conventional EEG analysis. *Electroencephalogr Clin Neurophysiol.* 106, 206-212 (1998).
Edgar D M, Dement W C, Fuller C A. Effect of SCN lesions on sleep in squirrel monkeys: evidence for opponent processes in sleep-wake regulation. J Neurosci. 1993 13:1065-79.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

A number of embodiments of the invention have been described. Nevertheless, it can be understood that various modifications may be made without departing from the spirit and scope of embodiments as described herein. Accordingly, other embodiments are within the scope of the following claims.

What is claimed is:

1. A pharmaceutical composition formulated as an an eye drop or an eye ointment comprising a compound ((3R)-1-(4-Fluoro-3-methoxybenzyl)-N-(9-chloro-3,4-dihydro-2H-1,5-benzodioxepin-7-ylmethyl)-N-isobutylpyrrolidine-3-carboxamide, or a stereoisomer thereof, or a pharmaceutically acceptable salt thereof, wherein the compound comprises a structure:

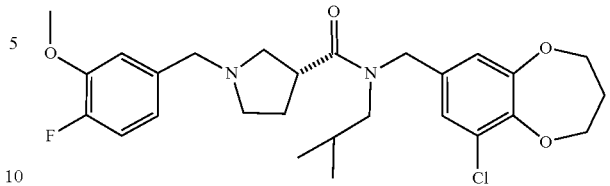

wherein the compound, stereoisomer thereof, or pharmaceutically acceptable salt thereof acts as a PK2 antagonist, or is capable of decreasing activity of or de-activating prokineticin 2 (PK2), or acting as a PK2 receptor antagonist.

2. A kit comprising: a pharmaceutical composition of claim 1.

3. A product of manufacture comprising: a pharmaceutical composition of claim 1.

4. The pharmaceutical composition of claim 1, formulated as a semi-solid, liquid or emulsion formulation.

5. The pharmaceutical composition of claim 1, wherein the compound is formulated as nanoparticles or nanolipoparticles.

6. The product of manufacture of claim 3, wherein the product of manufacture is a pump, a device, a needle, a reservoir, an ampoule, a vial, a syringe, a cartridge, a pen, jet injector, a syringe, a cartridge or a jet injector.

7. The product of manufacture of claim 6, wherein the pen is an infusion pen, a prefilled pen or a disposable pen.

8. The product of manufacture of claim 6, wherein the pump is a multi-chambered pump or a two chambered pump.

9. The pharmaceutical composition of claim 1, wherein the eye drop or an eye ointment consists essentially of the compound ((3R)-1-(4-Fluoro-3-methoxybenzyl)-N-(9-chloro-3,4-dihydro-2H-1,5-benzodioxepin-7-ylmethyl)-N-isobutylpyrrolidine-3-carboxamide.

* * * * *